(12) United States Patent
Yaegashi et al.

(10) Patent No.: US 8,430,652 B2
(45) Date of Patent: Apr. 30, 2013

(54) BLOOD PUMP APPARATUS

(75) Inventors: Mitsutoshi Yaegashi, Ashigarakami-gun (JP); Takehiko Asada, Ashigarakami-gun (JP); Takehisa Mori, Ashigarakami-gun (JP); Takayoshi Ozaki, Iwata (JP); Kenichi Suzuki, Iwata (JP)

(73) Assignees: Terumo Kabushiki Kaisha, Shibuya-Ku, Tokyo (JP); NTN Corporation, Osaka-Shi, Osaka (JP)

( * ) Notice: Subject to any disclaimer, the term of this patent is extended or adjusted under 35 U.S.C. 154(b) by 71 days.

(21) Appl. No.: 12/781,254

(22) Filed: May 17, 2010

(65) Prior Publication Data

US 2010/0221130 A1  Sep. 2, 2010

Related U.S. Application Data

(62) Division of application No. 11/087,851, filed on Mar. 24, 2005, now Pat. No. 7,748,964.

(30) Foreign Application Priority Data

Mar. 24, 2004 (JP) .................................. 2004-088108
Mar. 31, 2004 (JP) .................................. 2004-103573

(51) Int. Cl.
  *F04B 17/03* (2006.01)
(52) U.S. Cl.
  USPC ...................................... 417/423.12; 417/420
(58) Field of Classification Search .................. 417/420, 417/423.12
  See application file for complete search history.

(56) References Cited

U.S. PATENT DOCUMENTS 3,620,638 A  11/1971  Kaye
3,663,074 A  5/1972  Fernlund et al.
(Continued)

FOREIGN PATENT DOCUMENTS

EP  0 971 212 A1  1/2000
EP  1 113 177 A2  7/2001
(Continued)

OTHER PUBLICATIONS

Official Action issued on Sep. 13, 2011 by the Japanese Patent Office in corresponding Japanese Patent Application No. 2009-069148, and partial English language translation of the Official Action.

(Continued)

*Primary Examiner* — Charles Freay
(74) *Attorney, Agent, or Firm* — Buchanan Ingersoll & Rooney PC

(57) ABSTRACT

A blood pump apparatus comprises a housing, a centrifugal pump section including an impeller and rotating inside the housing to feed a fluid by a centrifugal force, an impeller rotational torque generation section for attracting thereto said impeller and rotating said impeller; and a plurality of grooves for hydrodynamic bearing provided on an inner surface of said housing at a side of said impeller rotational torque generation section, each of the grooves for hydrodynamic bearing having a first side and a second side both extending from a periphery of said portion in which a groove for hydrodynamic bearing is formed toward a central side thereof and opposed to each other, a third side connecting one end of said first side and one end of said second side to each other, and a fourth side connecting said other end of said first side and said other end of said second side to each other; said first side and said second side are formed as a circular arc respectively in such a way that centers of said circular arcs are different from each other.

11 Claims, 26 Drawing Sheets

U.S. PATENT DOCUMENTS

| | | | |
|---|---|---|---|
| H0974 H | 11/1991 | Mizobuchi et al. | |
| 5,350,283 A * | 9/1994 | Nakazeki et al. | 417/423.7 |
| 5,798,454 A | 8/1998 | Nakazeki et al. | |
| 5,947,703 A * | 9/1999 | Nojiri et al. | 417/420 |
| 6,071,093 A * | 6/2000 | Hart | 417/424.2 |
| 6,493,181 B1 | 12/2002 | Ichiyama et al. | |
| 6,634,224 B1 | 10/2003 | Schöb et al. | |
| 6,840,735 B2 | 1/2005 | Yaegashi et al. | |
| 2001/0016170 A1 | 8/2001 | Ozaki et al. | |
| 2003/0152462 A1 | 8/2003 | Yaegashi et al. | |
| 2004/0143151 A1 | 7/2004 | Mori et al. | |
| 2004/0236420 A1 | 11/2004 | Yamane et al. | |
| 2005/0008496 A1 | 1/2005 | Tsubouchi et al. | |

FOREIGN PATENT DOCUMENTS

| | | |
|---|---|---|
| EP | 1 327 455 A1 | 7/2003 |
| EP | 1 430 919 A | 6/2004 |
| EP | 1 495 773 A2 | 1/2005 |
| JP | 4-91396 | 3/1992 |
| JP | 4-112994 A | 4/1992 |
| JP | 4-209995 A | 7/1992 |
| JP | 7-279880 A | 10/1995 |
| JP | 07-509156 A | 10/1995 |
| JP | 8-042563 A | 2/1996 |
| JP | 09-206372 A | 8/1997 |
| JP | 09-206374 A | 8/1997 |
| JP | 2002-70866 A | 3/2002 |
| JP | 2002-227795 A | 8/2002 |
| JP | 2002-349468 A | 12/2002 |
| JP | 2003-024434 A | 1/2003 |
| JP | 2003-201992 A | 7/2003 |
| JP | 2004-52998 A | 2/2004 |
| WO | WO 94/02187 A1 | 2/1994 |
| WO | WO 00/64509 A1 | 11/2000 |

OTHER PUBLICATIONS

Jean Frene et al, "Hydrodynamic Lubrication, Bearings and Thrust Bearings", 1997, pp. 72-77, Tribology Series 33, Elsevier, The Netherlands.

Partial European Search Report issued in corresponding European Patent Application No. 05 00 6391, EPO, Munich, DE.

European Search Report issued in corresponding European Patent Application No. 05 00 6391, EPO, Munich, DE.

Official Action issued in corres. JP 2004-088108, Jan. 27, 2009, Japan Patent Office, JP; and partial English-language translation thereof.

Official Action issued in corres. JP 2004-103573, Jan. 27, 2009, Japan Patent Office, JP; and partial English-language translation thereof.

* cited by examiner

38

BLOOD PUMP APPARATUS

CROSS-REFERENCE TO RELATED APPLICATIONS

This application is a divisional of U.S. application Ser. No. 11/087,851 filed on Mar. 24, 2005 and which claims priority to Japanese Application Nos, 2004-88108 filed on Mar. 24, 2004 and 2004-103573 filed on Mar. 31, 2004, the entire contents of which are incorporated herein by reference.

BACKGROUND OF THE PRESENT INVENTION

In recent medical treatment, centrifugal blood pumps are increasingly used in artificial heart/lung units for extracorporeal blood circulation. Centrifugal pumps of the magnetic coupling type wherein a driving torque from an external motor is transmitted to an impeller through magnetic coupling are commonly used because the physical communication between the blood chamber of the pump and the exterior can be completely excluded and invasion of bacteria can be prevented.

The turbo-type pump disclosed in Japanese Patent Application Laid-Open No. 4-91396 (patent document 1) is described below as an example of the centrifugal blood pump. In the turbo-type pump disclosed therein, the magnetic coupling is formed by the first permanent magnet provided at one side of the impeller and the second permanent magnet opposed to the first permanent magnet through the housing. The rotor on which the second permanent magnet is mounted is rotated. Thereby the impeller is attracted toward the rotor with the impeller rotating. The impeller is spaced at a small interval from the inner surface of the housing owing to the hydrodynamic bearing effect generated between the groove for hydrodynamic bearing and the inner surface of the housing. Thus impeller rotates without contacting the housing.

In the hydrodynamic bearing pump, the fluid-feeding impeller is kept out of contact with peripheral surfaces of surrounding parts by a load-carrying capacity (load-carrying capacity is a term of a bearing and has dimension of force) generated by the groove for hydrodynamic bearing and a force resisting to the load-carrying capacity, for example, a magnetic force. Thereby hemolysis and thrombus are prevented from occurring.

The load-carrying capacity varies according to the configuration of the groove for hydrodynamic bearing. That is, the distance between the impeller and the surrounding parts varies according to the configuration of the groove for hydrodynamic bearing. Therefore the designing of the configuration of the groove for hydrodynamic bearing is important.

In the conventional groove for hydrodynamic bearing, the principal object is to increase the load-carrying capacity. Thus a logarithmic spiral groove is conventionally adopted. However, it is important to prevent the hemolysis to a high extent in addition to making the load-carrying capacity high.

It is a first object of the present invention to provide a centrifugal blood pump apparatus not of a type of magnetically levitating an impeller but allowing a rotation of the impeller without substantial contact between the impeller and a housing by utilizing a groove for hydrodynamic bearing and preventing occurrence of hemolysis to a high extent during use.

In the hydrodynamic bearing pump, the fluid-feeding impeller is kept out of contact with peripheral surfaces of surrounding parts by a load-carrying capacity (load-carrying capacity is a term of a bearing and has dimension of force) generated by the groove for hydrodynamic bearing and a force resisting to the load-carrying capacity, for example, a magnetic force. Thereby hemolysis and thrombus are prevented from occurring.

The present applicant proposed the centrifugal fluid pump apparatus as disclosed in U.S. Pat. No. 6,840,735 (patent document 2). The centrifugal fluid pump apparatus 1 has the control mechanism 6 and the pump body 5 including the pump section 2 having the impeller 21 rotating in the housing 20; the rotor 31 having a magnet 33 for attracting the impeller 21 thereto; a motor 34 for rotating the rotor 31; the electromagnet 41 for attracting the impeller 21 thereto, the sensor 42 for detecting the position of the impeller 21, and the groove 38 for hydrodynamic bearing provided on the inner surface of the housing 20. The control mechanism 6 has the position sensor output monitoring function 56, the electromagnet current monitoring function 57, and the motor current monitoring function.

Whether the sensor has a failure is determined by using the position sensor output monitoring function 56. Whether the electromagnet has a failure is determined by using by using the electromagnet current monitoring function 57. The centrifugal fluid pump apparatus 1 further includes the emergency impeller rotation function that operates when the failure detection function has detected that the sensor or the electromagnet has a failure to rotate the impeller 21 by utilizing the groove 38 for hydrodynamic bearing.

In the hydrodynamic pressure bearing pump, the impeller is kept out of contact with the housing in blood. However, in the pump apparatus disclosed in the patent document 1, it is impossible to find the position of the impeller. Thus it is impossible to check whether the impeller is rotating without contacting the inner surface of the housing with a predetermined interval kept between the impeller and the inner surface of the housing. The groove for hydrodynamic bearing of the pump apparatus disclosed in the patent document 2 is used for an emergency such as the failure of the sensor and not of the type of rotating the impeller by always using the hydrodynamic pressure generated by the groove for hydrodynamic bearing. The sensor does not measure the position of the impeller when the impeller is rotated without contacting the housing by the hydrodynamic pressure generated by the groove for hydrodynamic bearing.

It is a second object of the present invention to provide a centrifugal blood pump apparatus not of a type of magnetically levitating an impeller but allowing a rotation of the impeller without substantial contact between the impeller and a housing by utilizing a groove for hydrodynamic bearing and allowing the position of the impeller to be checked.

SUMMARY OF THE PRESENT INVENTION

The first object described above is attained by the following a centrifugal fluid pump apparatus.

A centrifugal blood pump apparatus comprises a housing having a blood inlet port and a blood outlet port; a centrifugal pump section including an impeller having a magnetic material and rotating inside said housing to feed a fluid by a centrifugal force generated during a rotation thereof; an impeller rotational torque generation section for attracting thereto said impeller of said centrifugal pump section and rotating said impeller; and a portion, in which a groove for hydrodynamic bearing is formed, provided on an inner surface of said housing at a side of said impeller rotational torque generation section or a surface of said impeller at said side of said impeller rotational torque generation section, said impeller being rotated by said groove for hydrodynamic bearing without contacting said housing, wherein a plurality of grooves for hydrodynamic bearing is formed on said portion in which a groove for hydrodynamic bearing is formed; each of said grooves for hydrodynamic bearing has a first side and a second side both extending from a periphery of said portion in which a groove for hydrodynamic bearing is formed toward a central side thereof and opposed to each other, a third side connecting one end of said first side and one end of said second side to each other, and a fourth side connecting said other end of said first side and said other end of said second side to each other; said first side and said second side are formed as a circular arc respectively in such a way that centers of said circular arcs are different from each other; a value relating to a groove depth ratio a ($a=h1/h2$) computed from a distance h1 between said impeller and said housing in said groove for hydrodynamic bearing of said portion in which a groove for hydrodynamic bearing is formed during a rotation of said impeller and from a distance h2 between said impeller and said housing in a hydrodynamic bearing groove-non-present portion of said portion in which a groove for hydrodynamic bearing is formed during said rotation of said impeller is in a range of 1.5 to 2.5; and a value relating to a groove width ratio s ($s=B_0/B$) computed from a width $B_0$ of a peripheral portion of each groove for hydrodynamic bearing and a sum B ($B=B_0+B1$) of said width $B_0$ and a width B1 of a hydrodynamic bearing groove-non-present portion between peripheral portions of adjacent grooves for hydrodynamic bearing is in a range of 0.6 to 0.8.

Further, the first object described above is attained by the following a centrifugal fluid pump apparatus.

A centrifugal blood pump apparatus comprises a housing having a blood inlet port and a blood outlet port; a centrifugal pump section including an impeller having a magnetic material and rotating inside said housing to feed a fluid by a centrifugal force generated during a rotation thereof; an impeller rotational torque generation section for attracting thereto said impeller of said centrifugal pump section and rotating said impeller; and a portion, in which a groove for hydrodynamic bearing is formed, provided on an inner surface of said housing at a side of said impeller rotational torque generation section or a surface of said impeller at a side of said impeller rotational torque generation section, said impeller being rotated by said groove for hydrodynamic bearing without contacting said housing, wherein a plurality of grooves for hydrodynamic bearing is formed on said portion in which a groove for hydrodynamic bearing is formed; each of said grooves for hydrodynamic bearing has a first side and a second side both extending from a periphery of said portion in which a groove for hydrodynamic bearing is formed toward a central side thereof and opposed to each other, a third side connecting one end of said first side and one end of said second side to each other, and a fourth side connecting said other end of said first side and said other end of said second side to each other; said first side and said second side are formed as a circular arc respectively in such a way that centers of said circular arcs are different from each other; and four corners composed of said four sides are rounded.

The second object described above is attained by the following a centrifugal fluid pump apparatus.

A blood pump apparatus comprises a housing having a blood inlet port and a blood outlet port; a pump section including an impeller having a magnetic material disposed therein and rotating in said housing to feed blood; and an impeller rotational torque generation section for attracting thereto said impeller of said pump section and rotating said impeller, wherein said pump section further comprises a groove for hydrodynamic bearing provided on an inner surface of said housing at a side of said impeller rotational torque generation section or a surface of said impeller at said side of said impeller rotational torque generation section, said impeller being rotated by said groove for hydrodynamic bearing without contacting said housing, wherein said pump section further comprises a sensor for measuring a position of said impeller when said impeller is rotated without contacting said housing by a hydrodynamic pressure generated by said groove for hydrodynamic bearing.

BRIEF DESCRIPTION OF THE DRAWINGS

The above and other objects, features and advantages of the present invention will be better understood by reading the following description, taken in conjunction with the accompanying drawings.

DETAILED DESCRIPTION OF THE PREFERRED EMBODIMENTS

Figure 1:
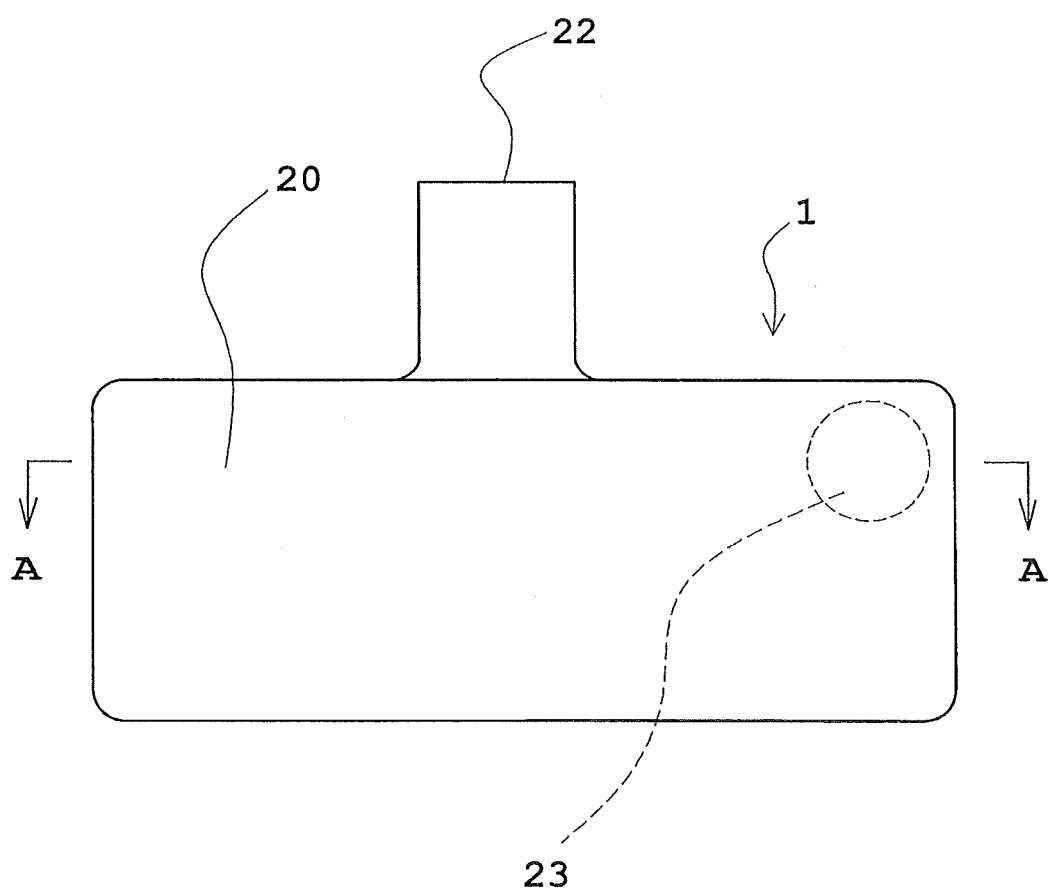
FIG. 1 is a front view showing a centrifugal blood pump apparatus according to an embodiment of the present invention.
Figure 2:
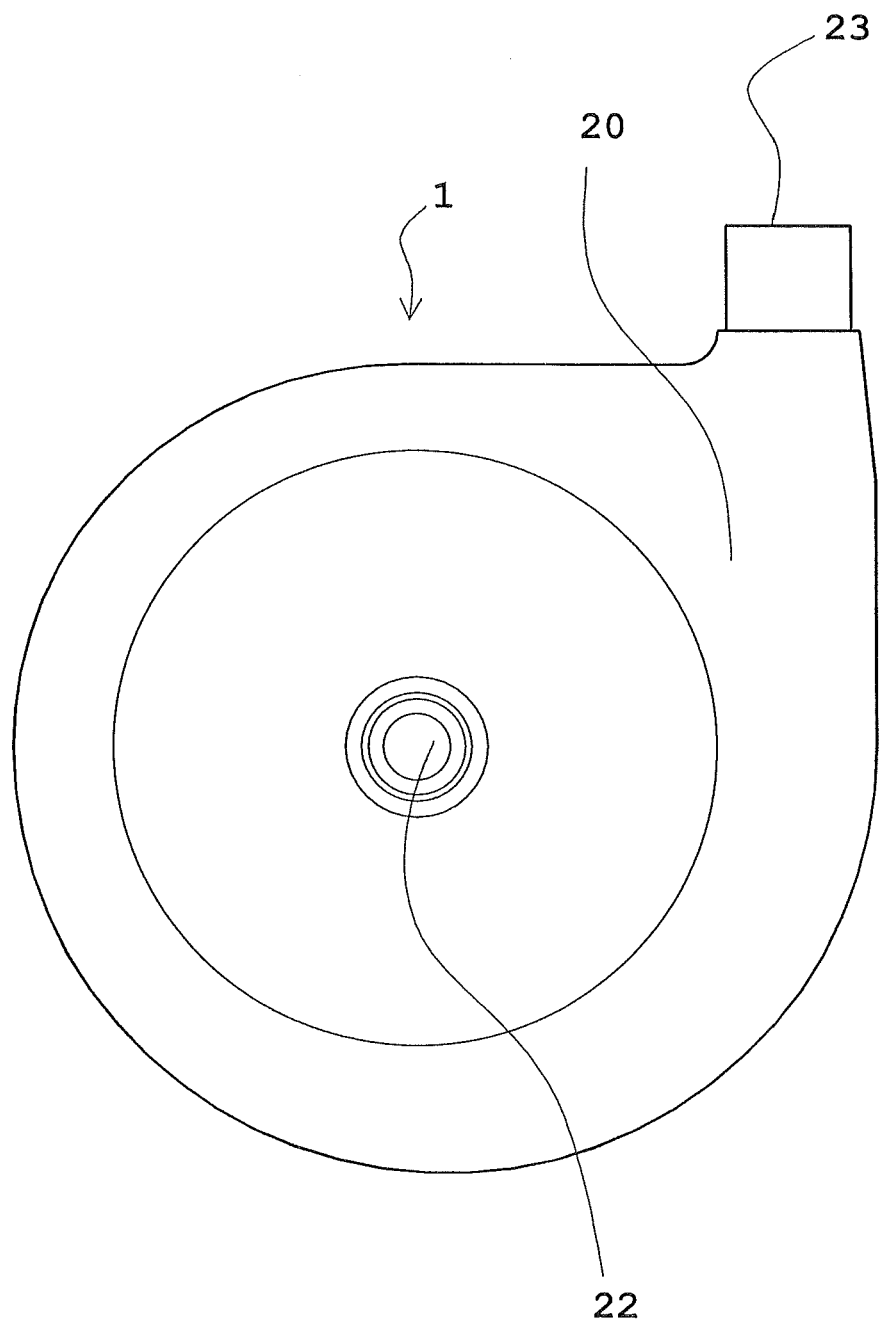
FIG. 2 is a plan view showing the centrifugal blood pump apparatus shown in FIG. 1.
Figure 3:
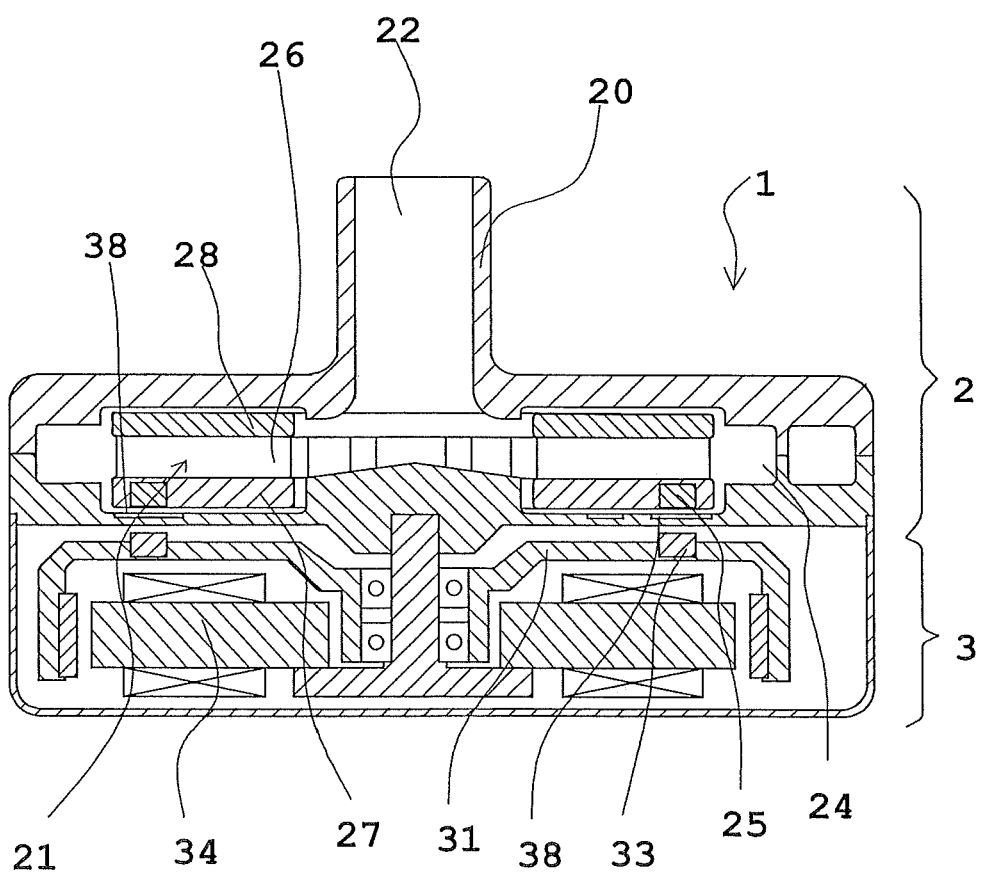
FIG. 3 is a vertical sectional view showing the centrifugal blood pump apparatus of the embodiment shown in FIG. 1.
Figure 4:
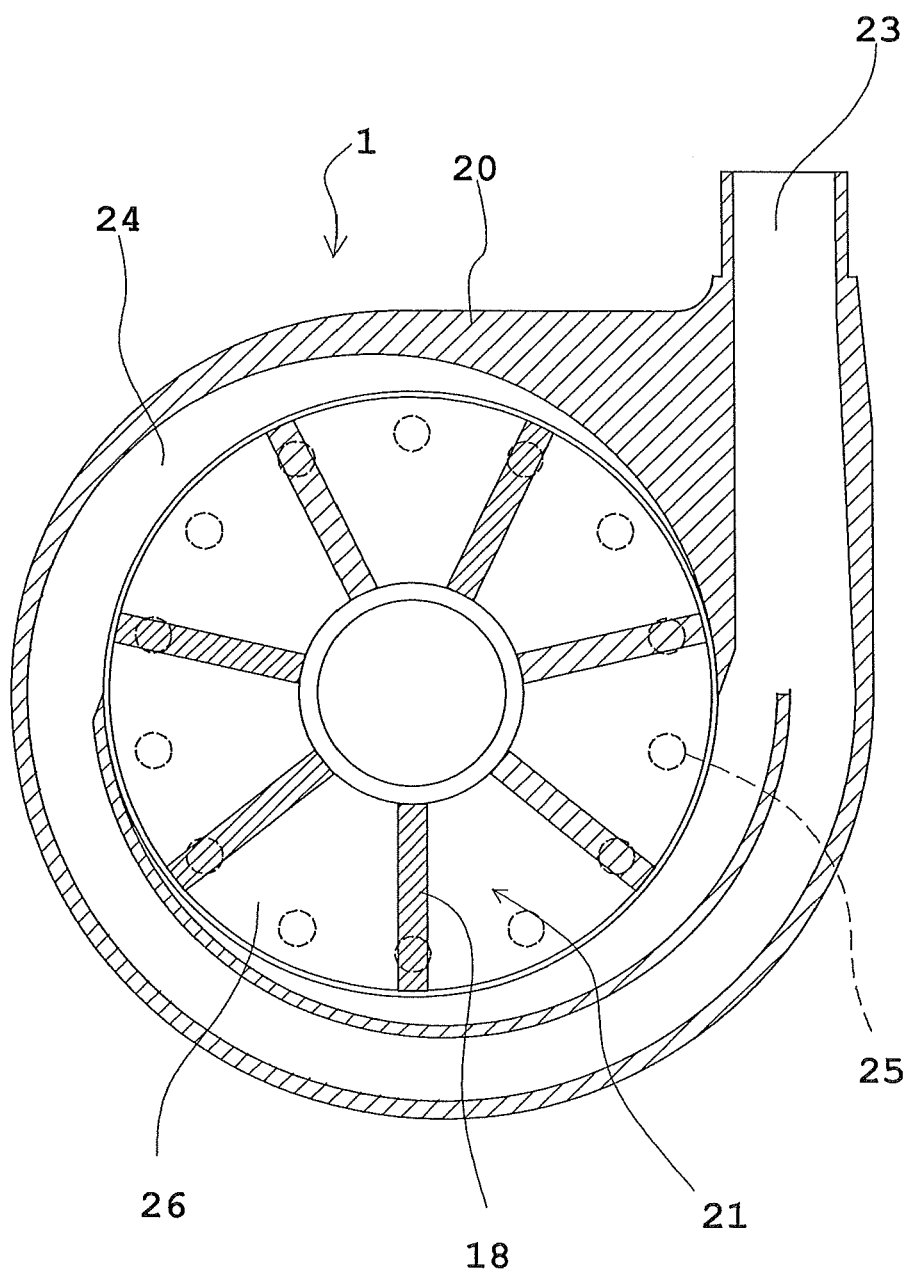
FIG. 4 is a sectional view, taken along a line A-A in FIG. 1, showing the centrifugal blood pump apparatus.
Figure 5:
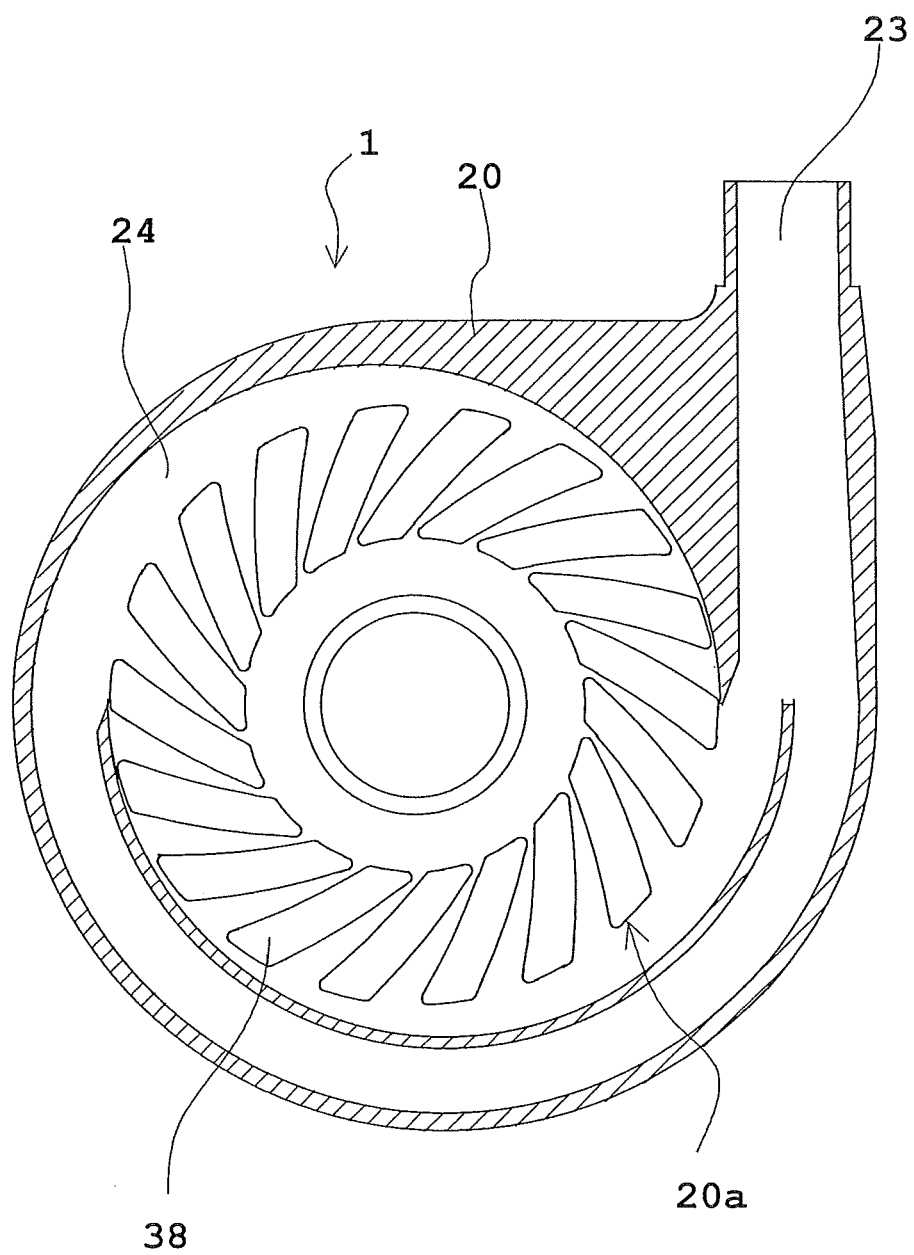
FIG. 5 is a sectional view showing a state in which an impeller is removed from the sectional view, taken along a line A-A in FIG. 1, showing the centrifugal blood pump apparatus.

FIG. 1 is a front view showing a centrifugal blood pump apparatus according to an embodiment of the present invention. FIG. 2 is a plan view showing the centrifugal blood pump apparatus shown in FIG. 1. FIG. 3 is a vertical sectional view showing the centrifugal blood pump apparatus of the embodiment shown in FIG. 1. FIG. 4 is a sectional view, taken along a line A-A in FIG. 1, showing the centrifugal blood pump apparatus. FIG. 5 is a sectional view showing a state in which an impeller is removed from the sectional view, taken along a line A-A in FIG. 1, showing the centrifugal blood pump apparatus.

A centrifugal blood pump apparatus 1 of the present invention includes a housing 20 having a blood inlet port 22 and a blood outlet port 23; a centrifugal pump section 2 including an impeller 21 having a magnetic material 25 disposed therein and rotating inside the housing 20 to feed a fluid by a centrifugal force generated during its rotation; an impeller rotational torque generation section 3 for attracting thereto the magnetic material 25 of the impeller 21 of the centrifugal pump section 2 and rotating the impeller 21; and a groove 38 for hydrodynamic bearing (hereinafter referred to as hydrodynamic bearing groove) provided on an inner surface of the housing 20 at the side of the impeller rotational torque generation section 3 thereof or a surface of the impeller 21 at the side of the impeller rotational torque generation section 3 thereof. In the centrifugal blood pump apparatus 1, the impeller 21 is rotated by the hydrodynamic bearing groove 38 without contacting the housing 20.

In a first aspect of the centrifugal blood pump apparatus of the present invention, each hydrodynamic bearing groove 38 has a first side 38a and a second side 38b both extending from the periphery of a portion 39 in which a groove for hydrodynamic bearing is formed toward the central side thereof and opposed to each other, a third side 38c connecting one end of the first side 38a and one end of the second side 38b to each other, and a fourth side 38d connecting the other end of the first side 38a and the other end of the second side 38b to each other. The first side 38a and the second side 38b are formed as a circular arc respectively in such a way that the centers of the circular arcs are different from each other. A value relating to a groove depth ratio a (a=h1/h2) computed from a distance h1 between the impeller 21 and the housing 20 in the hydrodynamic bearing groove of the portion in which a hydrodynamic bearing groove is formed during a rotation of the impeller 21 and from a distance h2 between the impeller 21 and the housing 20 in the hydrodynamic bearing groove-non-present portion (in other words, land region) of the portion in which a hydrodynamic bearing groove is formed during the rotation of the impeller 21 is in the range of 1.5 to 2.5. The hydrodynamic bearing groove-non-present portion is said in other words as land region. A value relating to a groove width ratio s (s=$B_0$/B) computed from a width $B_0$ of a peripheral portion of each hydrodynamic bearing groove and a sum B (B=$B_0$+B1) of the width $B_0$ and a width B1 of a hydrodynamic bearing groove-non-present portion between peripheral portions of adjacent grooves for hydrodynamic bearing is in a range of 0.6 to 0.8.

Therefore the hydrodynamic bearing groove 38 is capable of obtaining a load-carrying capacity almost equal to that of a logarithmic groove for hydrodynamic bearing. In addition since the hydrodynamic bearing groove 38 is wider and shallower than the logarithmic groove for hydrodynamic bearing having the same number of grooves, the hydrodynamic bearing groove 38 generates a less amount of hemolysis.

In a second aspect of the centrifugal fluid pump apparatus of the present invention, the hydrodynamic bearing groove 38 has the first side 38a and the second side 38b both extending from the periphery of the portion 39 thereof in which a hydrodynamic bearing groove is formed toward the central side thereof and opposed to each other, the third side 38c connecting one end of the first side 38a and one end of the second side 38b to each other, and the fourth side 38d connecting the other end of the first side 38a and the other end of the second side 38b to each other. The first side 38a and the second side 38b are formed as the circular arc respectively in such a way that the centers of the circular arcs are different from each other. In addition, four corners 38e, 38f, 38g, and 38h composed of the four sides 38a, 38b, 38c, and 38d are rounded.

The area of the hydrodynamic bearing groove whose corners are rounded is smaller than the hydrodynamic bearing groove whose corners are not rounded, although the load-carrying capacity of the corner-rounded hydrodynamic bearing grooves decreases slightly. In addition, the corner-rounded hydrodynamic bearing groove does not have a portion where a pressure is excessively high. Thereby the corner-rounded hydrodynamic bearing groove gives a smaller damage to blood than the hydrodynamic bearing groove whose corners are not rounded and further causes blood to stagnate to a lower extent than the hydrodynamic bearing groove whose corners are not rounded. Therefore the corner-rounded hydrodynamic bearing groove causes generation of hemolysis and thrombus to a lower extent than the hydrodynamic bearing groove whose corners are not rounded because the former causes blood to stagnate to a lower extent than the latter.

The four corners of the hydrodynamic bearing groove are rounded at not less than 0.1 mm. Thereby the hydrodynamic bearing groove causes the hemolysis to occur to a lower extent.

It is preferable that the third side and the fourth side are formed as a circular arc respectively in such a way that the circular arcs have the same center and different radii. Thereby the hydrodynamic bearing groove is readily machinable.

It is preferable that the centrifugal blood pump apparatus 1 of the present invention has both the first and second aspects. The centrifugal blood pump apparatus will be described below by using an embodiment having both the first and second aspects.

In the centrifugal blood pump apparatus 1, the impeller is rotated not with the impeller magnetically levitated but with the impeller out of contact with the housing by means of the hydrodynamic bearing groove. This construction eliminates the need for an electromagnet occupying a larger area than other parts used for the magnetic levitation of the impeller. Thus it is possible to make the centrifugal blood pump apparatus compact.

As shown in FIGS. 1 through 5, the centrifugal blood pump apparatus 1 has the housing 20 having the blood inlet port 22 and the blood outlet port 23; the centrifugal pump section 2 having the impeller 21 rotating inside the housing 20 to feed blood by a centrifugal force generated during its rotation; and the impeller rotational torque generation section 3 for the impeller 21.

In the centrifugal blood pump apparatus 1 of this embodiment, the impeller rotational torque generation section 3 has a rotor 31 having a magnet 33 for attracting thereto the magnetic material 25 of the impeller 21; and a motor 34 for rotating the rotor 31.

As shown in FIG. 3, the impeller 21 rotates without contacting the inner surface of the housing 20 by a pressure generated by the hydrodynamic bearing groove 38 when the impeller 21 rotates.

The housing 20 has the blood inlet port 22 and the blood outlet port 23 and is formed of a non-magnetic material. The housing 20 accommodates a blood chamber 24 communicating with the blood inlet port 22 and the blood outlet port 23. The housing 20 also accommodates the impeller 21 therein. The blood inlet port 22 projects substantially vertically from the vicinity of the center of the upper surface of the housing 20. The blood inlet port 22 does not necessarily have to be formed as a straight pipe, but may be formed as a curved pipe or a bent pipe. As shown in FIGS. 2 and 4, the blood outlet port 23 projects tangentially from the side surface of the approximately cylindrical housing 20.

As shown in FIG. 3, the disc-shaped impeller 21 having a through-hole in the center thereof is accommodated inside the blood chamber 24 formed inside the housing 20. As shown in FIGS. 3 and 4, the impeller 21 includes an annular plate-shaped member (lower shroud) 27 forming the lower surface thereof, an annular plate-shaped member (upper shroud) 28 forming the upper surface thereof and opening at the center thereof, and a plurality of (for example, seven) vanes 18 formed between the lower shroud 27 and the upper shroud 28. A plurality of (for example, seven) blood passages 26 partitioned from one another by the adjacent vanes 18 is formed between the lower shroud 27 and the upper shroud 28. As shown in FIG. 4, each of the blood passages 26 communicates with the center opening of the impeller 21 and extends from the center opening of the impeller 21 to its periphery, with each of the blood passages 26 becoming gradually larger in the width thereof. In other words, the vanes 18 are formed between the adjacent blood passages 26. In the embodiment, the vanes 18 and blood passages 26 are spaced at equiangular intervals respectively and formed in substantially the same shape respectively.

As shown in FIGS. 3 and 4, a plurality (for example, 10 to 40) of the magnetic materials 25 (for example permanent magnet, follower magnet) are embedded in the impeller 21. In the embodiment, the magnetic materials 25 are embedded in the lower shroud 27 of the impeller 21. A permanent magnet 33, to be described later, provided in the rotor 31 of the rotational torque generation section 3 attracts the magnetic material 25 embedded in the impeller 21 toward the side opposite to the side where the blood inlet port 22 is disposed to allow the impeller 21 and the rotor 31. In this operation, the magnetic material 25 serves as a means for allowing to be magnetically coupled to each other and transmitting the rotational torque from the rotational torque generation section 3 to the impeller 21.

The magnetic coupling, to be described later, between the impeller 21 and the rotor 31 is ensured by embedding a plurality of the magnetic materials 25 (permanent magnet) in the impeller 21. It is preferable that each of the magnetic materials 25 is circular.

As shown in FIG. 3, the rotational torque generation section 3 has the rotor 31 accommodated in the housing 20 and the motor 34 for rotating the rotor 31. The rotor 31 has a plurality of permanent magnets 33 disposed on a surface thereof at the side of the centrifugal pump section 2. The center of the rotor 31 is fixedly secured to the rotational shaft of the motor 34. A plurality of the permanent magnets 33 is equiangularly distributed in accordance with the arrangement mode (number and position) of the permanent magnets 25 of the impeller 21.

In the coupling between the permanent magnet of the impeller and that of the motor, it is preferable to dispose the permanent magnet in such a way that an attractive force is generated between the impeller and the motor even though they are uncoupled from each other by an external force and a power swing occurs therebetween. Thereby even though the impeller and the motor are uncoupled from each other and the power swing occurs therebetween, they can be coupled to each other easily again because the attractive force is present therebetween.

Figure 6:
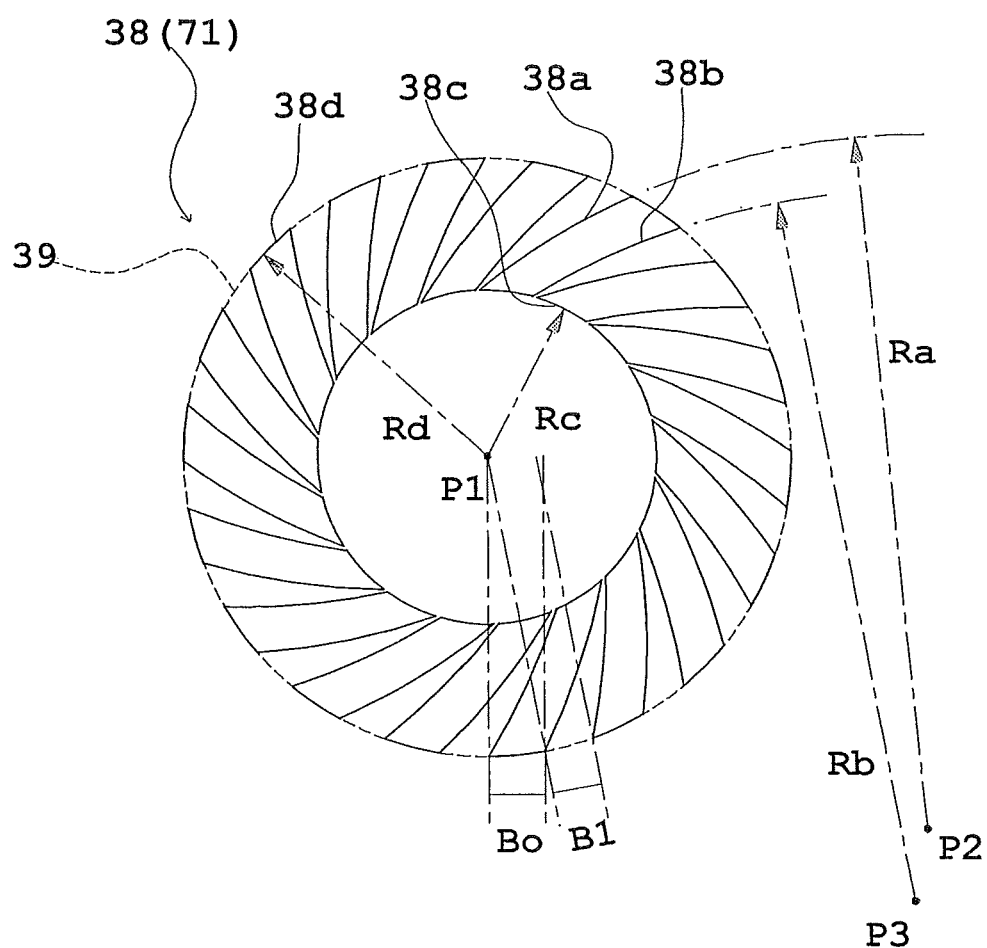
FIG. 6 is an explanatory view for explaining the mode of a groove for hydrodynamic bearing of the centrifugal blood pump apparatus of the present invention.

As shown in FIG. 6, in the centrifugal blood pump apparatus 1 of the embodiment, the housing 20 accommodates the impeller 21 and has the groove 38 for hydrodynamic bearing formed on an inner surface 20a of the housing 20, at the rotor-disposed side, forming the blood chamber 24. A hydrodynamic bearing effect generated between the groove 38 for hydrodynamic bearing and the impeller 21 by a rotation of the impeller 21 at a speed more than a predetermined number of rotations allows the impeller 21 to rotate without contacting the inner surface of the housing 20.

As shown in FIG. 6, the groove 38 for hydrodynamic bearing has a size corresponding to that of the bottom surface (surface at rotor side) of the impeller 21. In the centrifugal blood pump apparatus 1 of the embodiment, the groove 38 for hydrodynamic bearing extends spirally (in other words, curved) outwardly to the vicinity of the outer edge of the inner surface 20a, with one end of the groove 38 for hydrodynamic bearing disposed on the periphery (circumference) of a circle spaced outward at a short distance from the center of the inner surface 20a of the housing 20 and with the width thereof becoming outwardly gradually larger. A plurality of the grooves 38 for hydrodynamic bearing has substantially the same configuration and is spaced at almost equal intervals. Each of the grooves 38 for hydrodynamic bearing is concavely formed. It is preferable that the depth thereof is in the range of 0.05 to 0.4 mm. The number of the groove 38 for hydrodynamic bearing is favorably in the range of 6 to 36 and more favorably in the range of 8 to 24. In the embodiment, 18 grooves 38 for hydrodynamic bearing are provided at equiangular intervals around the axis of the impeller 21.

The groove 38 for hydrodynamic bearing may be disposed on the rotor-side surface of the impeller 21 instead of disposing it at the housing side. It is preferable that the groove 38 for hydrodynamic bearing disposed on the rotor-side surface of the impeller 21 has the same construction as that of the groove 38 for hydrodynamic bearing disposed at the housing side.

The groove 38 for hydrodynamic bearing having the above-described construction is attracted toward the impeller torque generation section 3. Owing to the hydrodynamic bearing effect generated between the groove 38 for hydrodynamic bearing disposed on the housing and the bottom surface of the impeller 21 (or between the groove 38 for hydrodynamic bearing disposed on the impeller and the inner surface of the housing), the impeller 21 rotates without contacting the inner surface of the housing 20 with the impeller 21 levitating slightly from the inner surface of the housing 20, thus providing a blood passage between the lower surface of the impeller 21 and the inner surface of the housing 20. Thereby it is possible to prevent blood from staying therebetween and thrombus from occurring because the blood is prevented from staying therebetween.

In the pump apparatus 1, the hydrodynamic bearing groove 38 has the first side 38a and the second side 38b both extending from the periphery of the portion 39 thereof in which a hydrodynamic bearing groove is formed toward the central side thereof and opposed to each other, the third side 38c connecting one end of the first side 38a and one end of the second side 38b to each other, and the fourth side 38d connecting the other end of the first side 38a and the other end of the second side 38b to each other. The first side 38a and the second side 38b are formed as a circular arc respectively in such a way that the centers of the circular arcs are different from each other. In this embodiment, the first side 38a and the second side 38b are composed of a circular arc respectively in such a way that the circular arcs have different centers and radii. Instead, the hydrodynamic bearing groove may be composed of circular arcs having the same center and different radii or different centers and the same radius. But the hydrodynamic bearing groove composed of circular arcs having different centers and radii can be provided with a larger width in the peripheral portion of the portion thereof in which a hydrodynamic bearing groove is formed thereof than the hydrodynamic bearing groove composed of circular arcs having the same center and different radii or the hydrodynamic bearing groove composed of different centers and the same radius.

In this embodiment, the third side 38c and the fourth side 38d are formed as a circular arc respectively in such a way that the circular arcs have the same center and different radii.

With reference to FIG. 6, the first side 38a is formed as the circular arc having a radius Ra and a center disposed at a point P2 located outside the portion 39 in which a hydrodynamic bearing groove is formed. The second side 38b is formed as the circular arc having a radius Rb and a center disposed at a point P3 located outside the portion 39 in which a hydrodynamic bearing groove is formed. Although the radius Ra varies according to the size of the blood pump apparatus, the radius Ra is set to preferably in the range of 30 to 70 mm. Although the radius Rb varies according to the size of the blood pump apparatus, the radius Rb is set to preferably in the range of 30 to 70 mm. It is preferable that the distance between the points P2 and P3 is set to the range of 3 to 10 mm. The third side 38c is formed as the circular arc having a radius Rc and a center disposed at a center P1 of the portion 39 in which a hydrodynamic bearing groove is formed. The fourth side 38d is formed as the circular arc having a radius Rd and a center disposed at the center P1 of the portion 39 in which a hydrodynamic bearing groove is formed. Although the radius Rc varies according to the size of the blood pump apparatus, the radius Rc is set to preferably in the range of 6 to 18 mm. Although the radius Rd varies according to the size of the blood pump apparatus, the radius Rd is set to preferably in the range of 15 to 30 mm. It is preferable that the radius Rc is 0.3 to 0.8 times the radius Rd.

As shown in FIG. 6, the value relating to a groove width ratio s ($s=B_0/B$) computed from the width $B_0$ of the peripheral portion of each hydrodynamic bearing groove and the sum B ($B=B_0+B1$) of the width $B_0$ and the width B1 of the hydrodynamic bearing groove-non-present portion between (land region) the peripheral portions of the adjacent grooves for hydrodynamic bearing is in a range of 0.6 to 0.8.

Figure 7:
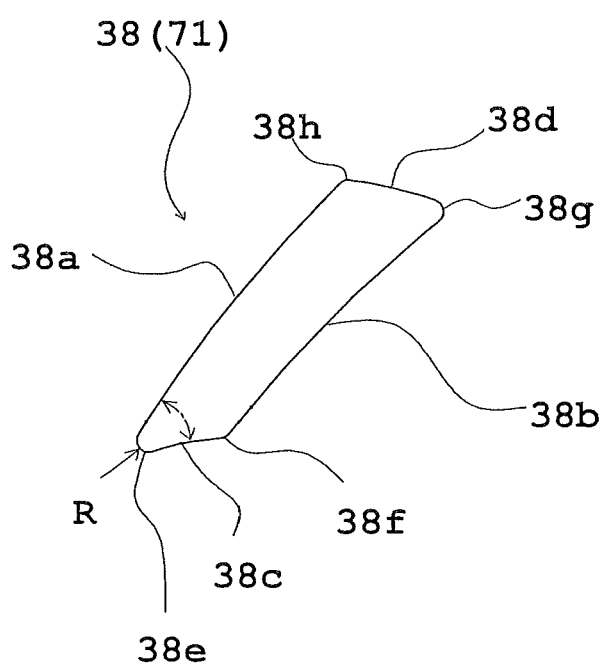
FIG. 7 is an explanatory view for explaining the mode of the groove for hydrodynamic bearing of the centrifugal blood pump apparatus of the present invention.

As shown in FIG. 7, in the pump apparatus of this embodiment, the hydrodynamic bearing groove 38 composed of the four sides 38a, 38b, 38c, and 38d, four corners 38e, 38f, 38g, and 38h are rounded. The four corners of said groove for hydrodynamic bearing are rounded at not less than 0.1 mm.

Figure 8:
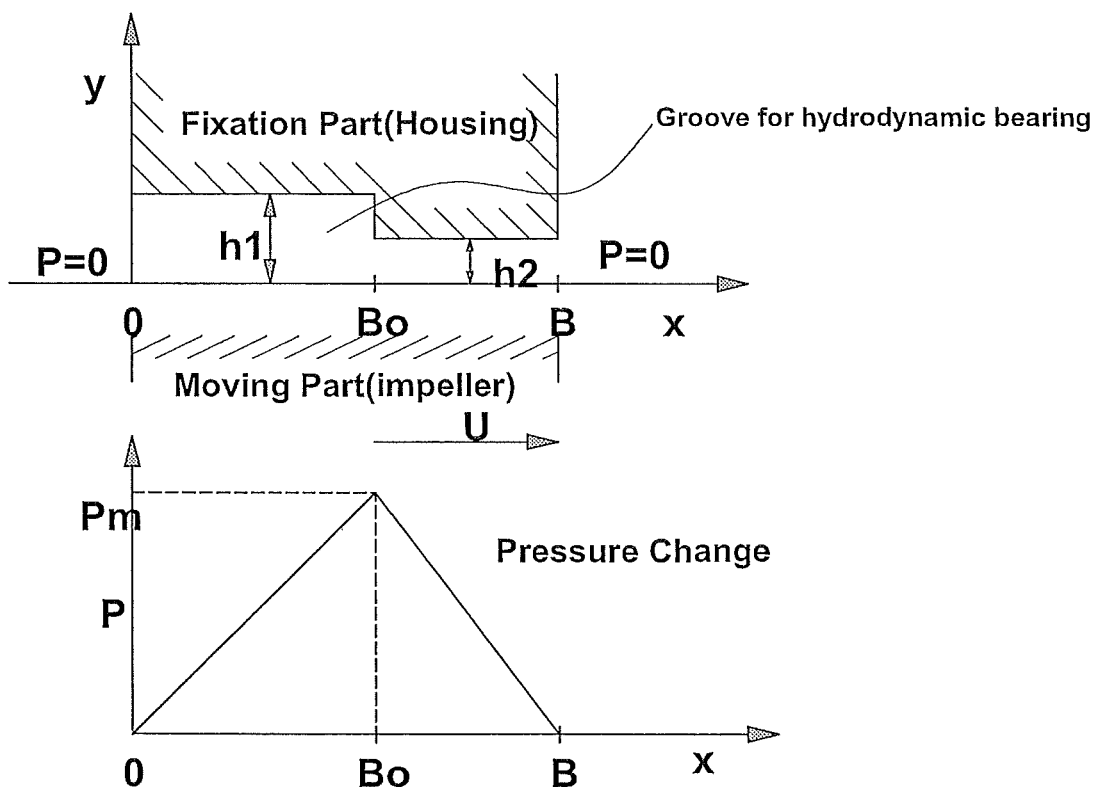
FIG. 8 is an explanatory view for explaining a two-dimensional theoretical analysis process regarding the groove for hydrodynamic bearing.

With reference to FIG. 8, the value relating to a groove depth ratio a ($a=h1/h2$) computed from the distance h1 between the impeller 21 and the housing 20 in the hydrodynamic bearing groove of the portion in which a hydrodynamic bearing groove is formed during the rotation of the impeller 21 and from the distance h2 between the impeller 21 and the housing 20 in the hydrodynamic bearing groove-non-present portion of the portion in which a hydrodynamic bearing groove is formed during the rotation of the impeller 21 is in the range of 1.5 to 2.5.

As described above, since the hydrodynamic bearing groove 38 is so constructed that the value relating to a groove width ratio s ($s=B_0/B$) is in the range of 0.6 to 0.8 and that the value relating to a groove depth ratio a ($a=h1/h2$) is in the range of 1.5 to 2.5, the hydrodynamic bearing groove 38 is wider and shallower than a logarithmic groove for hydrodynamic bearing having the same number of grooves. Thus the hydrodynamic bearing groove 38 generates a less amount of hemolysis.

Figure 14:
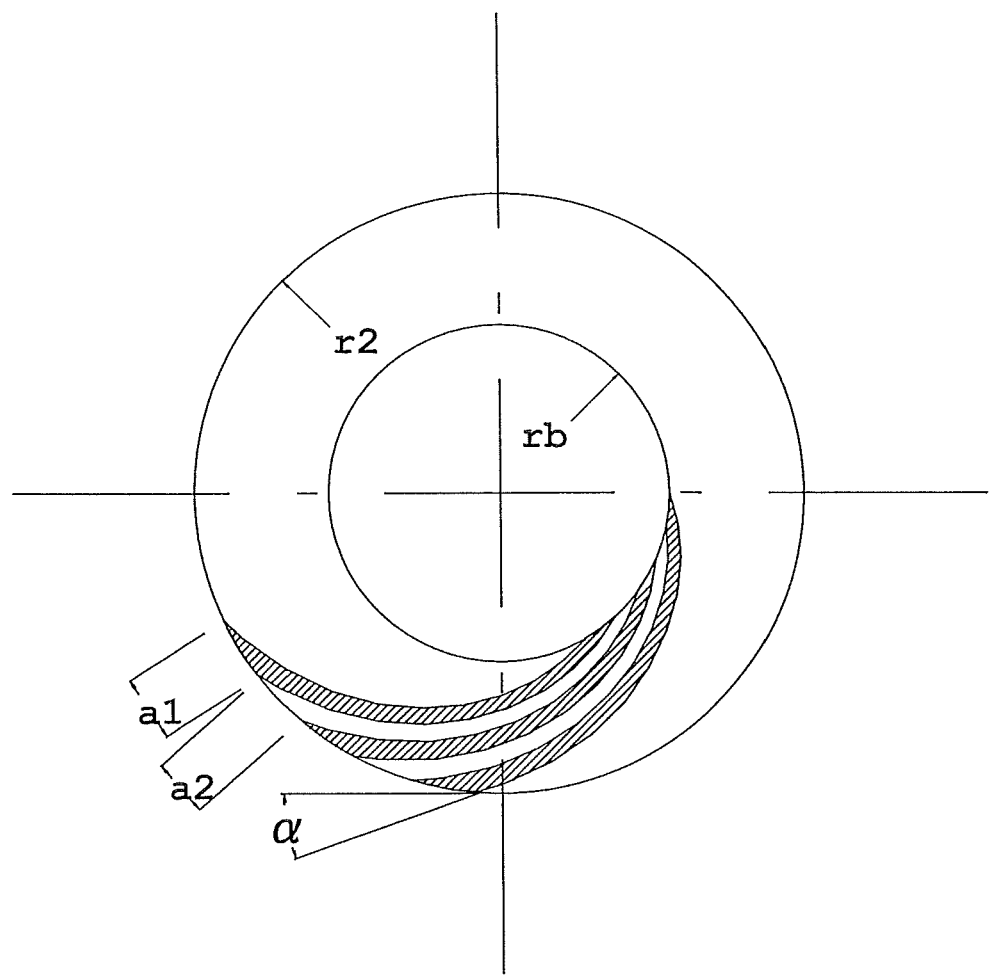
FIG. 14 is an explanatory view for explaining the mode of a groove for hydrodynamic bearing of a logarithmic spiral type.

In the case of a groove having the configuration of a logarithmic spiral groove shown in FIG. 14, the load-carrying capacity can be computed, supposing that the outer radius of the groove is r2, the inner radius thereof is rb, the fluid inlet angle of the groove is α, the ratio of the width of the groove to that of the land is a1/a2, the number of grooves is N, the depth of the groove is h1, the number of rotations is ω, and the viscosity is μ. For the hydrodynamic bearing groove having configurations other than the configuration shown in FIG. 14, appropriate parameters are determined by analyzing the flow of a fluid three-dimensionally and finding the load-carrying capacity or using results obtained by theoretically analyzing the flow of the fluid two-dimensionally (only sectional configuration of groove is considered and longitudinal dimension thereof orthogonal to the section thereof is considered to be sufficiently longer than sectional dimension). In this embodiment, the latter designing method is adopted.

In the centrifugal pump apparatus shown in FIG. 3, (1) A force of attracting the impeller toward the rotor is generated by the magnetic coupling between the impeller and the rotor.

(2) A force of moving the impeller toward the side opposite to the rotor side by the load-carrying capacity generated by the hydrodynamic bearing groove.

The impeller maintains its position without contacting the periphery thereof inside the housing with the force of (1) and that of (2) kept in balance.

Considering the hydrodynamic bearing groove having a configuration (length of hydrodynamic bearing groove in sectional direction is L) shown in FIG. 8, a pressure p is computed as follows:

In a region 1 ($0<x<B_o$): $p=(Pm/B_o)x$

In a region 2 ($B_o<x<B$): $p=[Pm/B-B_o)](B-x)$

A change of p in a y-direction is so small that the change can be ignored.

$Pm=6\mu U(h_1-h_2)/[h_1^3/B_o+h_2^3/(B-B_o)]$ where μ and U are the viscosity of the fluid and the speed (proportional to number of rotations) of the impeller in the radial direction.

Therefore, a load-carrying capacity W generated by one groove is shown as follows:

$$W = L \int_0^B p\,dx$$
$$= LBPm/2$$

Wd-less made dimensionless by dividing W by $\mu U L B^2 / h_2^2$ is shown as follows:

$$Wd\text{-}less = W h_2^2 / (\mu U L B^2)$$
$$= 3s(1-s)(a-1)/[a^3(1-s)+s]$$

where $a = h_1/h_2$, and $s = B_o/B$

Figure 9:
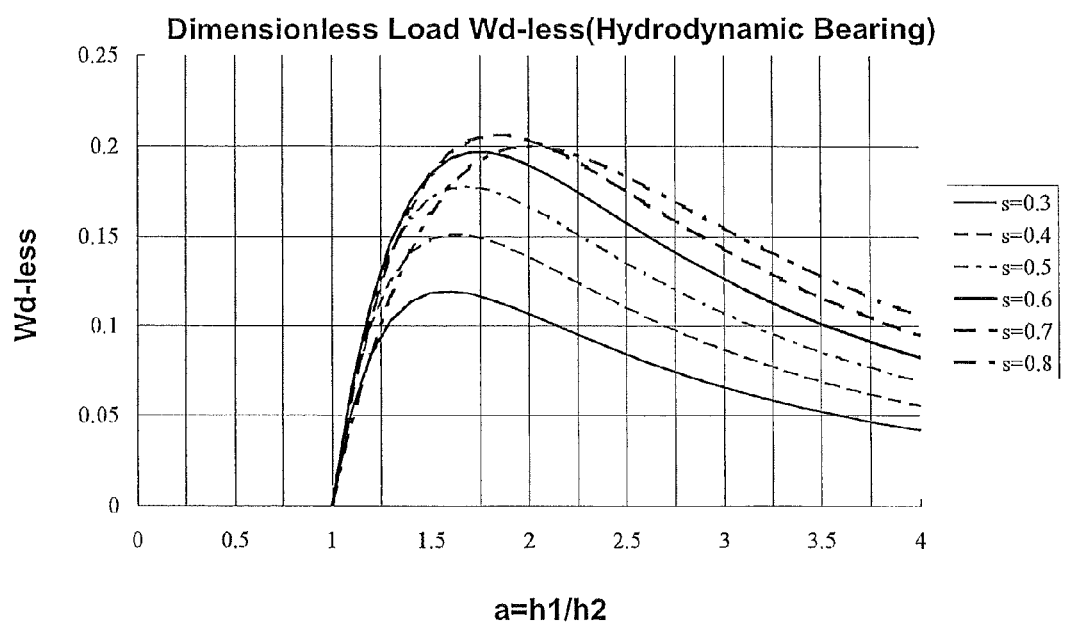
FIG. 9 is an explanatory view for explaining a two-dimensional theoretical analysis process regarding the groove for hydrodynamic bearing.

The change of Wd-less for a and s is as shown in FIG. 9. FIG. 9 indicates that there is (efficient) s ($B_o$/B) which provides a maximum load-carrying capacity for desired $h_1$ and $h_2$. Therefore it is possible to obtain a sufficient load-carrying capacity by appropriately setting $h_1$, $h_2$, B, $B_o$, and L which are parameters of the configuration of the hydrodynamic bearing groove.

FIG. 9 indicates that a=1.5 to 2.5 and s=0.6 to 0.8 fall in a practical range (value not less than 0.8 times maximum value).

In the case of the centrifugal pump, the outer and inner diameters of the impeller are designated. Thereby the outer and inner diameters of the groove are designated. Supposing that the diameter of the impeller is 50 mm, the outer diameter D2 of the groove D2=50 mm, and the inner diameter Db of the groove>20 mm, as the value relating to a groove depth ratio a and the value relating to a groove width ratio s, a=1.8 and s=0.65 are selected respectively to design the groove. The selection was made by setting the interval between adjacent grooves to not less than 0.5 mm.

When a=1.866 and s=0.7182, the load-carrying capacity is maximum. The values of Wd-less are 0.203 and 0.206 different by 1.5%, namely, almost equal. The impeller is desired to levitate by 0.1 mm (h2 in FIG. 8) by setting the value relating to a groove depth to 1.8. Thus the depth of the groove is 0.08 mm. In this case, a=1+0.08/0.1=1.8.

The procedure of designing the groove at the current time is shown below. FIG. 5 shows the final configuration of the groove.

(1) The outer diameter of the impeller is set to ϕ50. Thus the outer diameter of the groove is set to ϕ50.

(2) The inner diameter of the impeller is set to ϕ20. Thus the outer diameter of the groove can be set to not less than ϕ20.

The solution of (r2−rb)/(r2−r1) is aimed to be 0.7 to 0.8. Thus the inner radius of the groove rb is set to 14. In this case, the solution of (r2−rb)/(r2−r1)=0.73. Thereby two sides of the groove is determined.

(3) Thereafter a circle having a radius of 58 (unit: mm) is drawn with the center thereof disposed at a point (36, −31), when the center of the inner and diameters of the hydrodynamic bearing groove is disposed at the origin. The point (36, −31) and the radius 58 are designated from a desired fluid inlet angle (15 to 60 degrees) of the groove. Thereby three sides of the groove are determined. The midpoint between the radius 14 mm and the radius 25 mm is on the circumference of a circle having a diameter 19.5 mm. The angle formed between the x-axis and the point of intersection of the two circles is 72.36 degrees. Thus the coordinate of the point of intersection is (5.91, 18.58).

(4) Thereafter the width of the groove is determined so that s=0.65 on the circumference of a circle having a radius 19.5.

At the current time, the number of grooves is set to 18. Thus the grooves are formed at intervals of 20 degrees. When the diameter of the impeller (diameter of portion in which a hydrodynamic bearing groove is formed) is about 50 mm, it is appropriate that the number of the grooves is 15 to 20. When s=0.65, the angle of the groove is 20×0.65=13 degrees. Thus, from 72.36−13=59.36 degrees, the coordinate of the midpoint on the circumference opposed to the groove is (9.94, 16.78):

$$19.5 \cos(59.36°) = 9.94$$

$$19.5 \sin(59.36°) = 16.78$$

A circle whose radius is equal to the distance between this point and the point (35, −37) is drawn, with the center thereof disposed at a point (35, −37). Thereby the four sides of the groove are determined.

The point (35, −37) is designated in advance from the desired fluid inlet angle (15 to 60 degrees) of the groove.

(5) The four corners of the groove are rounded at R0.5. The four corners may be rounded at R1. When the four corners are rounded at a very generous radii, the load-carrying capacity becomes small. Supposing that a milling machine is used to machine the groove, it is proper that the four corners of the groove are rounded at R0.5 in view of the diameter of an end mill.

Figure 15:
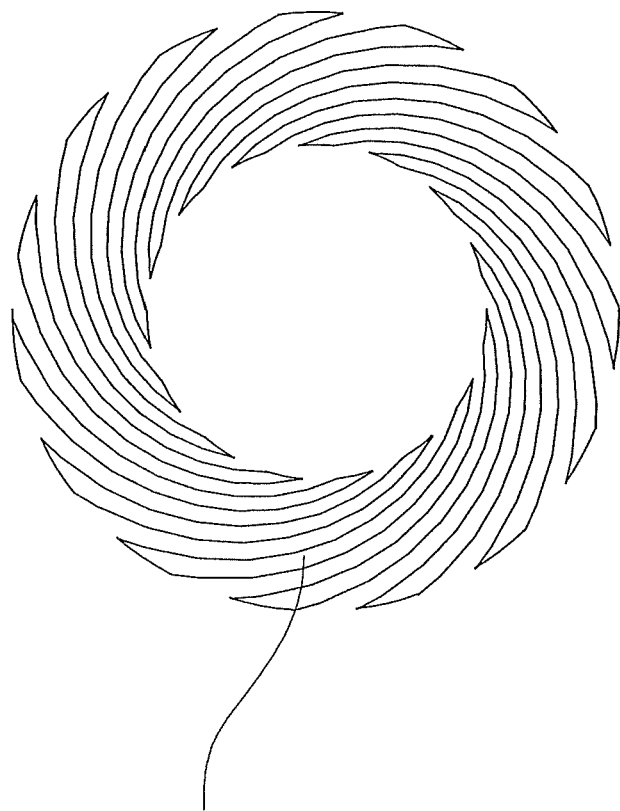
FIG. 15 is an explanatory view for explaining the mode of the groove for hydrodynamic bearing of the logarithmic spiral type.

(6) The grooves of 17 are drawn. FIG. 15 shows hydrodynamic bearing grooves designed in the same condition and same size as the above. The number of the grooves is slightly different from the above condition. By using the results of the designed hydrodynamic bearing grooves, measurement was conducted on a levitation amount (distance between impeller and land on surface of rotor) of the case in which the hydrodynamic bearing groove of the present invention was mounted on the pump (diameter of impeller: 40, 50 mm) having the construction shown in FIG. 3 and the case in which a conventional logarithmic spiral groove was mounted on the pump having the construction shown in FIG. 3 (in both cases, magnetic coupling force between impeller and rotor was set equally). As a result, the levitation amounts were equal to each other. This means that the load-carrying capacity generated by the hydrodynamic bearing groove of the present invention is equal to that generated by the conventional logarithmic spiral groove. Although the load-carrying capacities are equal to each other, the configuration of the hydrodynamic bearing groove of the present invention shown in FIG. 5 has the following advantages over the configuration of the conventional logarithmic spiral groove shown in FIG. 5.

(a) The configuration of the groove of the present invention allows its depth to be smaller and its width to be larger than that of the configuration of the conventional logarithmic spiral groove. This means that the configuration of the former gives a smaller damage to a red blood cell than that of the latter and advantageous over the latter in terms of hemolysis.

(b) As described above, the configuration of the former allows the depth of the groove to be smaller than that of the latter. This is advantageous in designing the hydrodynamic bearing groove. That is, in the case of the blood pump having the construction shown in FIG. 3, it is necessary to shorten the distance between the impeller and the rotor to some extent to secure the rigidity of the groove. This is because the force of the magnetic coupling between the impeller and the rotor is low when the distance therebetween is long. Consequently the rigidity deteriorates when the impeller levitates. Therefore there is a restriction on the thickness of the surface of the housing on which the hydrodynamic bearing groove is formed. It is necessary that the surface on which the hydrodynamic bearing groove is formed is strong because the motor is mounted thereon. As such it is possible to secure a desired strength for the surface on which the hydrodynamic bearing groove is formed by making the depth of the groove shallow. Further the shallow groove can be designed more easily than the deeper groove. In the construction shown in FIG. 3, the hydrodynamic bearing groove is formed only on the rotor-side surface of the housing. But it is conceivable to form the hydrodynamic bearing groove on the surface of the housing at the side of the blood inlet port to apply a hydrodynamic pressure to both surfaces of the impeller. In this case, there is no fear that the impeller and the rotor are magnetically uncoupled from each other owing to a large amount of movement of the impeller toward the blood inlet port caused by a great hydrodynamic pressure generated at the rotor side. As such it is possible to increase the levitation amount of the impeller when the impeller rotates at a low number of rotations by proving a magnetic coupling on the surface of the housing at the side of the blood inlet port. When the magnetic coupling is provided on the surface of the housing at the side of the blood inlet port, there is a restriction to the thickness of the surface of the housing at the side of the blood inlet port similarly to the restriction placed on the thickness of the on the rotor-side surface of the housing. In this respect, to make the hydrodynamic bearing groove shallow is advantageous in designing the hydrodynamic bearing groove.

A centrifugal blood pump apparatus according to another embodiment of the present invention is described below.

Figure 10:
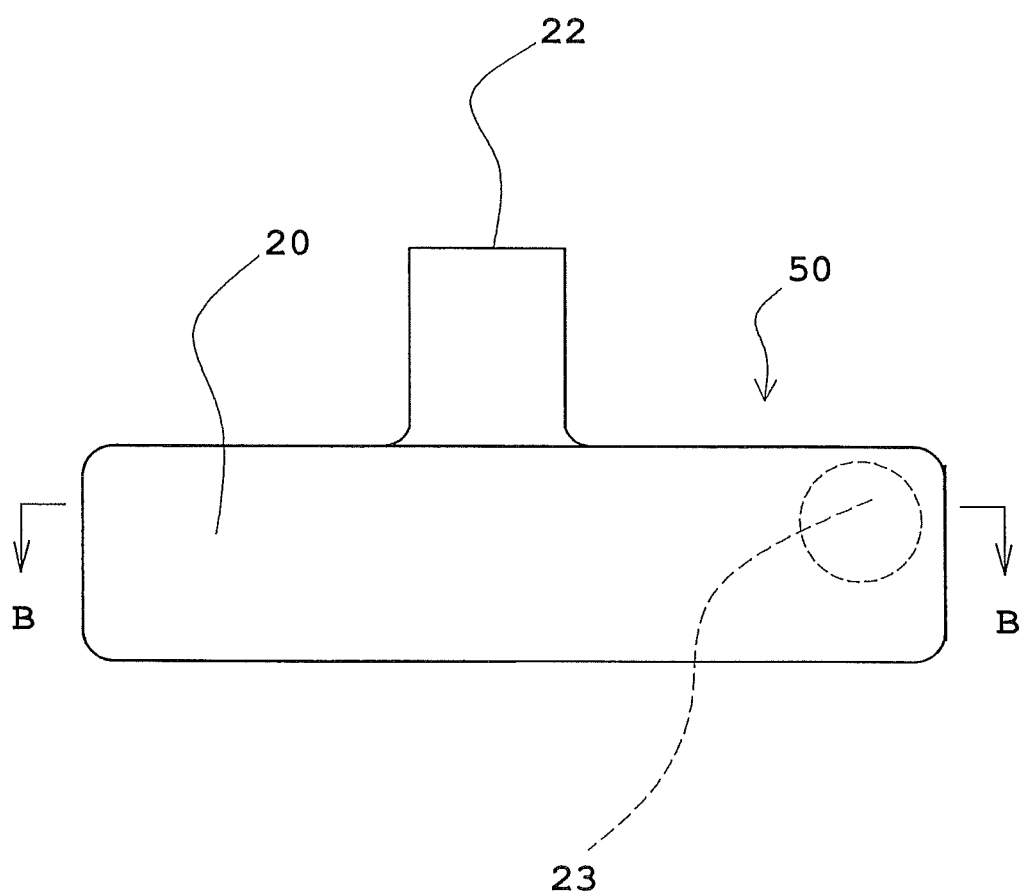
FIG. 10 is a front view showing a centrifugal blood pump apparatus according to another embodiment of the present invention.
Figure 11:
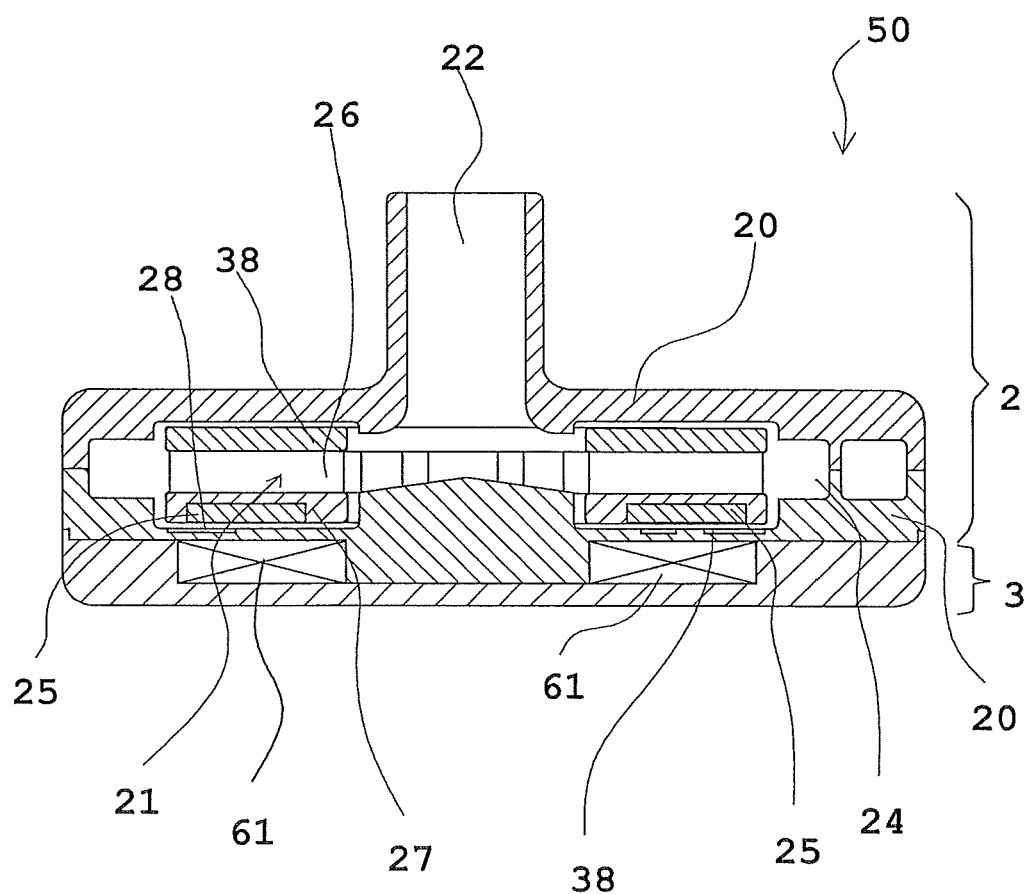
FIG. 11 is a vertical sectional view showing the centrifugal blood pump apparatus of the embodiment shown in FIG. 10.
Figure 12:
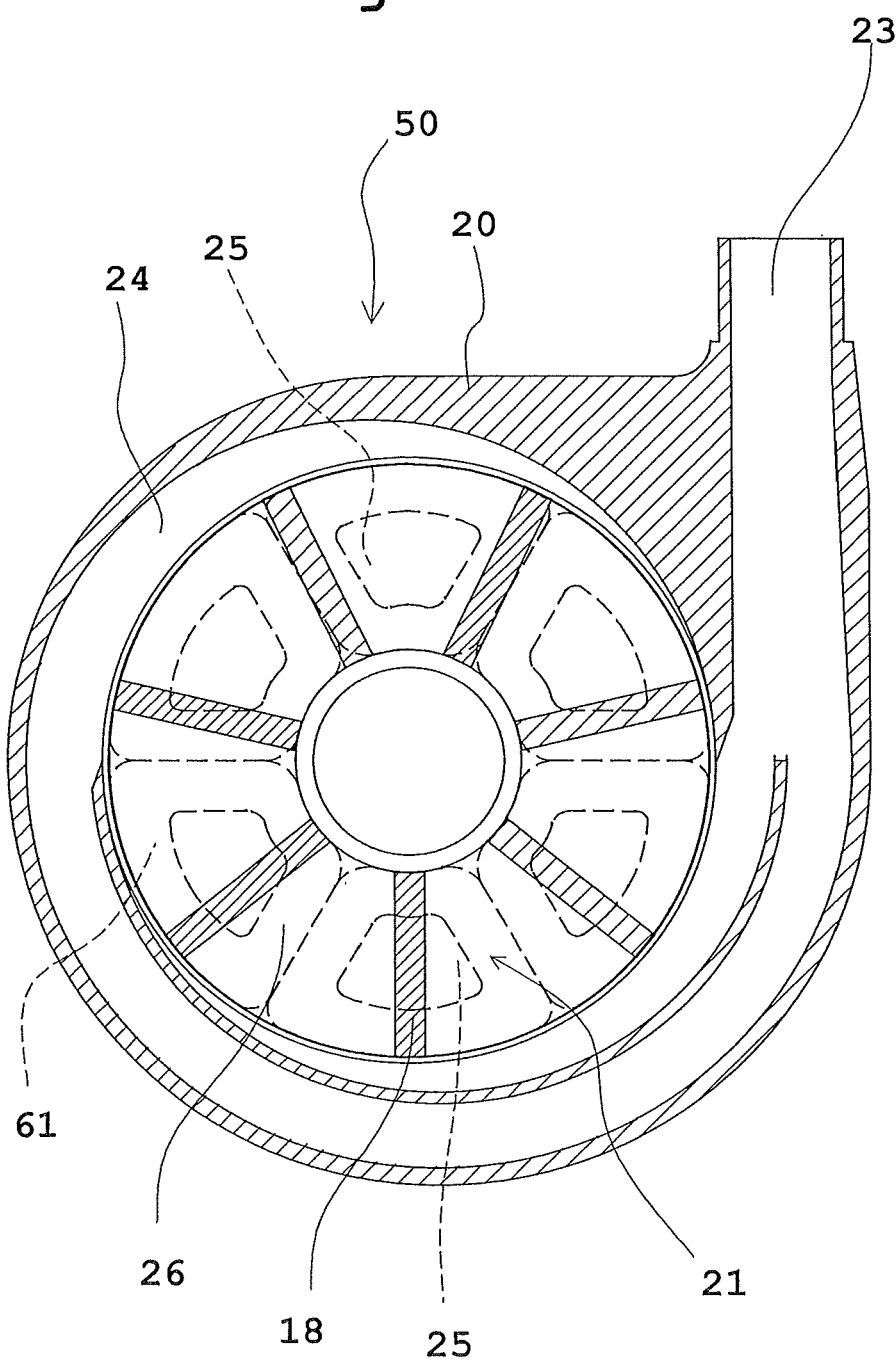
FIG. 12 is a sectional view, taken along a line B-B in FIG. 10, showing the centrifugal blood pump apparatus.
Figure 13:
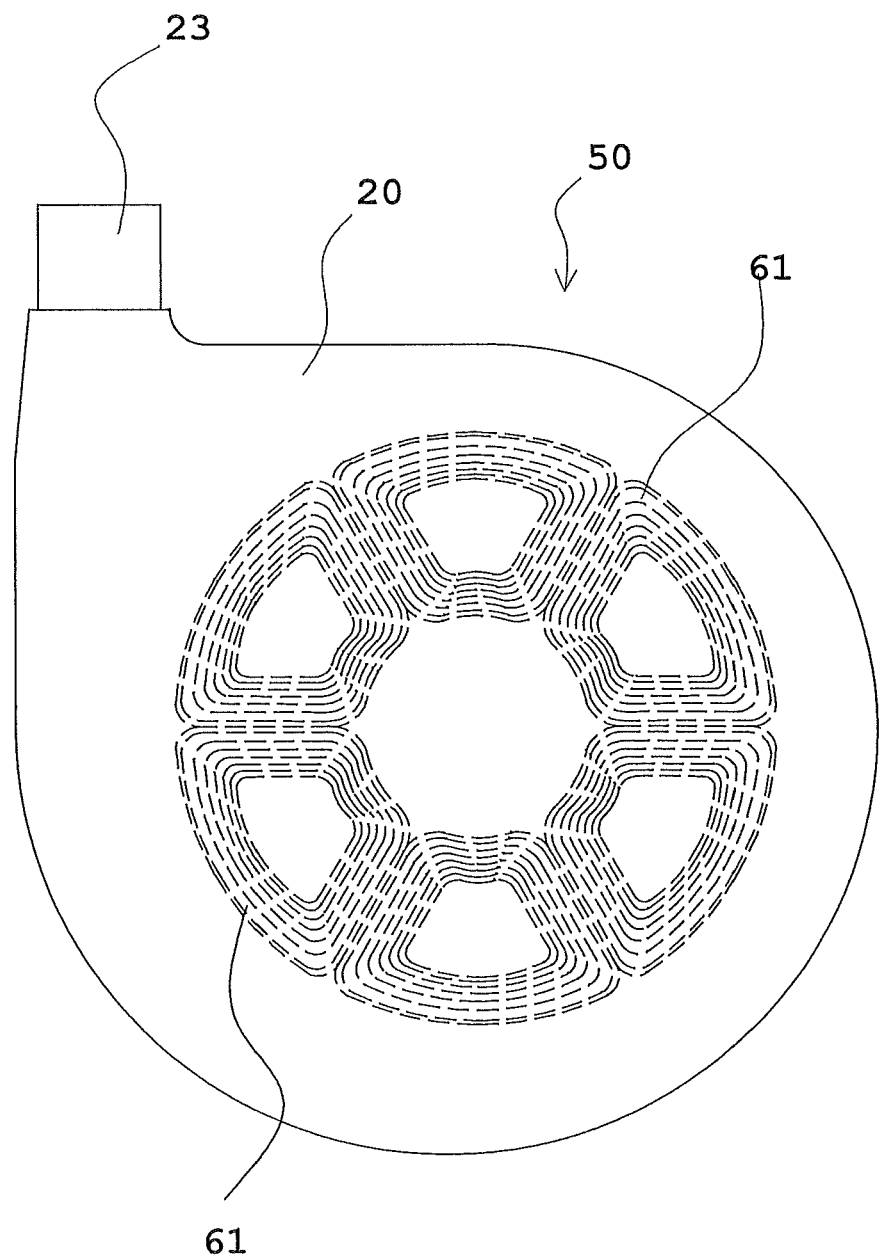
FIG. 13 is a bottom view showing the centrifugal blood pump apparatus shown in FIG. 10.

FIG. 10 is a front view showing a centrifugal blood pump apparatus according to another embodiment of the present invention. FIG. 11 is a vertical sectional view showing the centrifugal blood pump apparatus of the embodiment shown in FIG. 10. FIG. 12 is a sectional view, taken along a line B-B in FIG. 10, showing the centrifugal blood pump apparatus. FIG. 13 is a bottom view showing the centrifugal blood pump apparatus shown in FIG. 10. A plan view of the centrifugal blood pump apparatus according to the embodiment shown in FIG. 10 is the same as the plan view shown in FIG. 2. A sectional view showing the impeller removed from a sectional view taken along a line B-B in FIG. 10 is the same as the sectional view shown in FIG. 5. Therefore they are omitted herein.

A pump apparatus 50 of this embodiment is different from the pump apparatus 1 of the above-described embodiment in only the mechanism of the impeller rotational torque generation section 3. The impeller rotational torque generation section 3 of the pump apparatus 50 does not have a rotor, but is of a type of driving the impeller directly. In the pump apparatus 50 of this embodiment, the impeller 21 rotates without contacting the inner surface of the housing 20 by a pressure generated by the hydrodynamic bearing groove 38 when the impeller 21 rotates. In description that is described below, constructions different from those of the above-described embodiment are described. The mode of the hydrodynamic bearing groove 38 is the same as that of the above-described embodiment.

As shown in FIGS. 11, 12 and 13, the impeller rotational torque generation section 3 of the pump apparatus 50 has a plurality of stator coils 61 accommodated in the housing 20. The stator coils 61 are disposed along a circumference at equiangular intervals around the axis thereof. More specifically, six stator coils 61 are used. Multilayer stator coils are used as the stator coils 61. A rotating magnetic field is generated by switching the direction of electric current flowing through each stator coil 61. The impeller is attracted by the rotating magnetic field and rotates.

As shown in FIG. 12, a plurality (for example, 6 to 12) of the magnetic materials 25 (for example, permanent magnet, follower magnet) is embedded in the impeller 21. In the embodiment, the magnetic materials 25 are embedded in the lower shroud 27. The stator coils 61 provided in the rotational torque generation section 3 attracts the magnetic material 25 embedded in the impeller toward the side opposite to the side where the blood inlet port 22 is disposed. In this operation, the magnetic materials 25 couple to the operation of the stator coils 61 and transmit the rotational torque from the rotational torque generation section 3 to the impeller 21.

The magnetic coupling, to be described later, between the impeller 21 and the stator rotor 61 is ensured by embedding a plurality of the magnetic materials 25 (permanent magnet) in the impeller 21. It is preferable that each of the magnetic materials 25 is approximately trapezoidal. The magnetic materials 25 are ring-shaped or plate-shaped. It is preferable that the number and arrangement mode of the magnetic materials 25 correspond to those of the stator coils 61. The magnetic materials 25 are disposed circumferentially at equiangular intervals around the axis of the impeller in such a way that positive and negative poles thereof alternate with each other.

Figure 16:
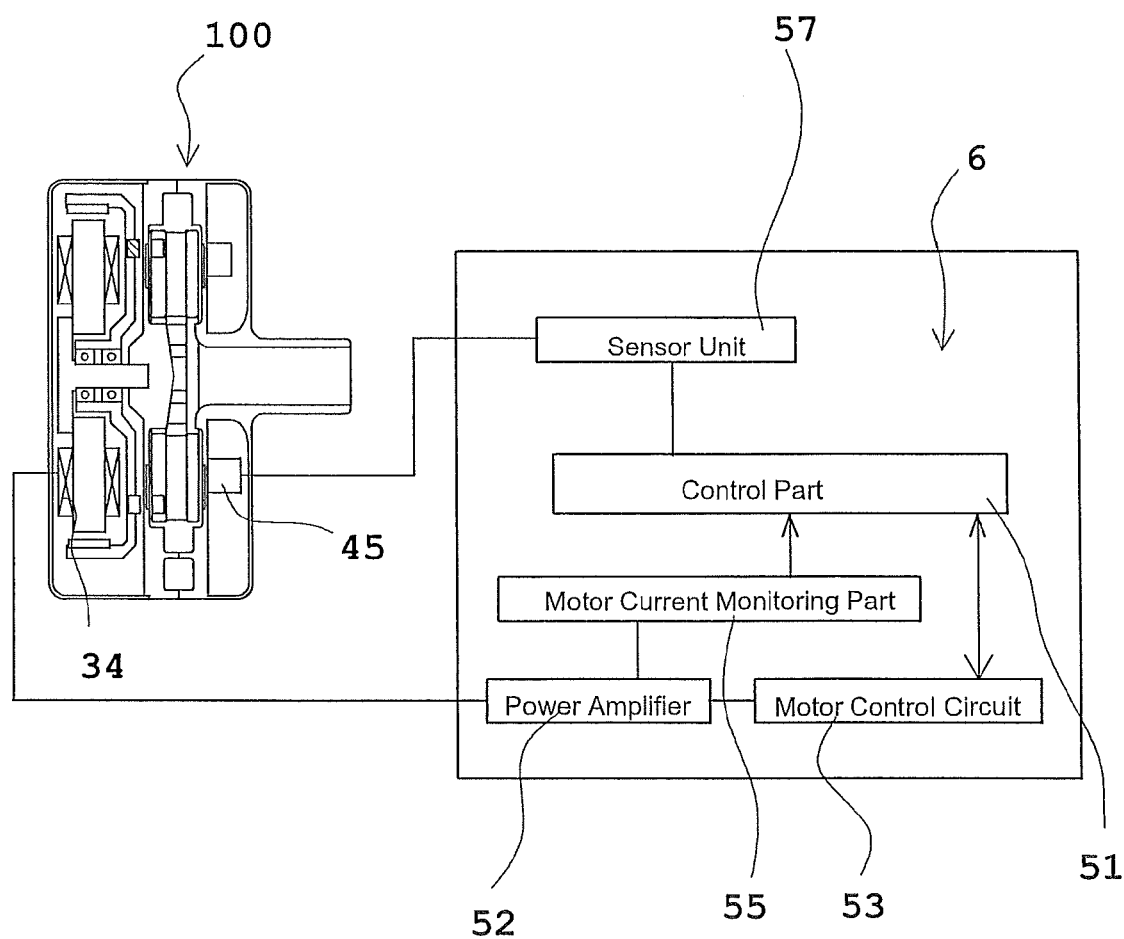
FIG. 16 is a block diagram of an embodiment including a control mechanism of a blood pump apparatus of the present invention.
Figure 17:
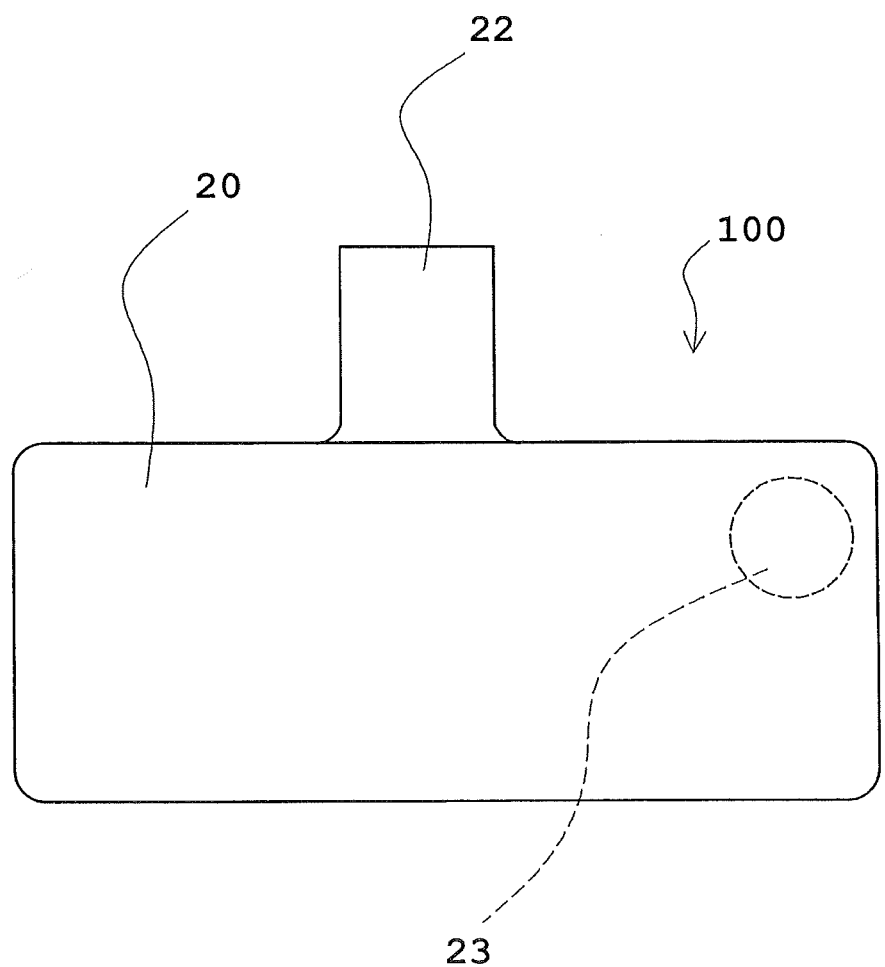
FIG. 17 is a front view showing a blood pump apparatus according to still another embodiment of the present invention.
Figure 18:
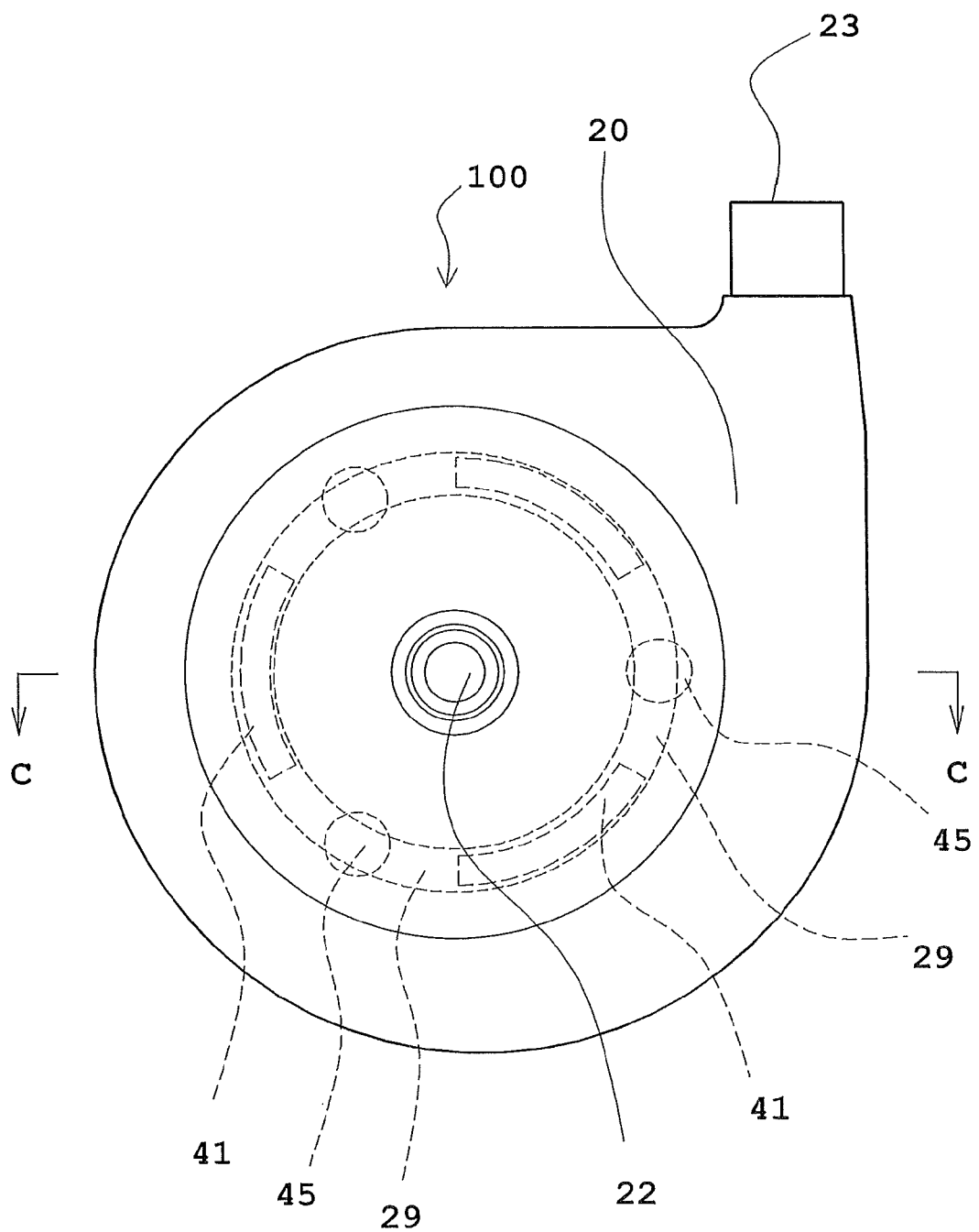
FIG. 18 is a plan view showing the blood pump apparatus shown in FIG. 17.
Figure 19:
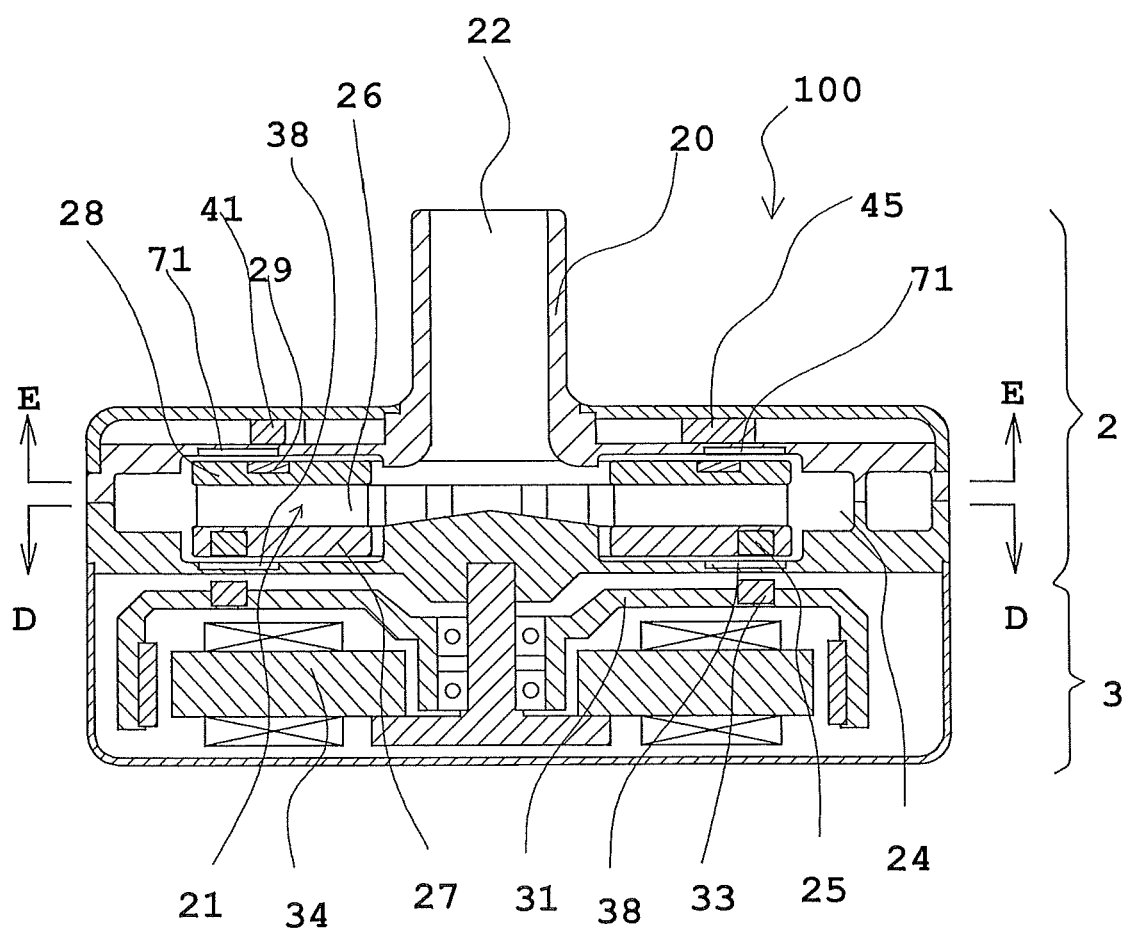
FIG. 19 is a sectional view taken along a line C-C in FIG. 18.
Figure 20:
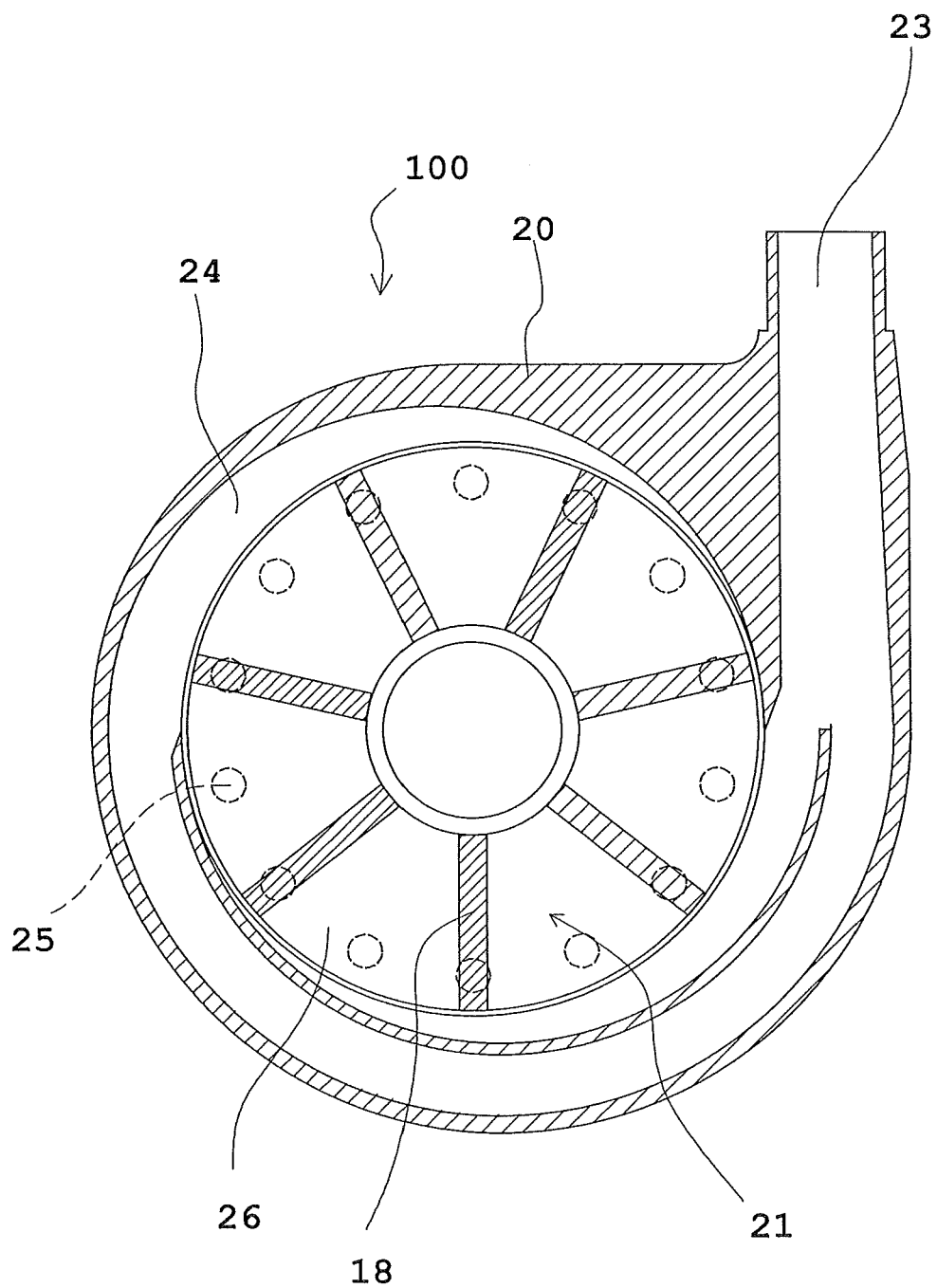
FIG. 20 is a sectional view taken along a line D-D in FIG. 19.
Figure 21:
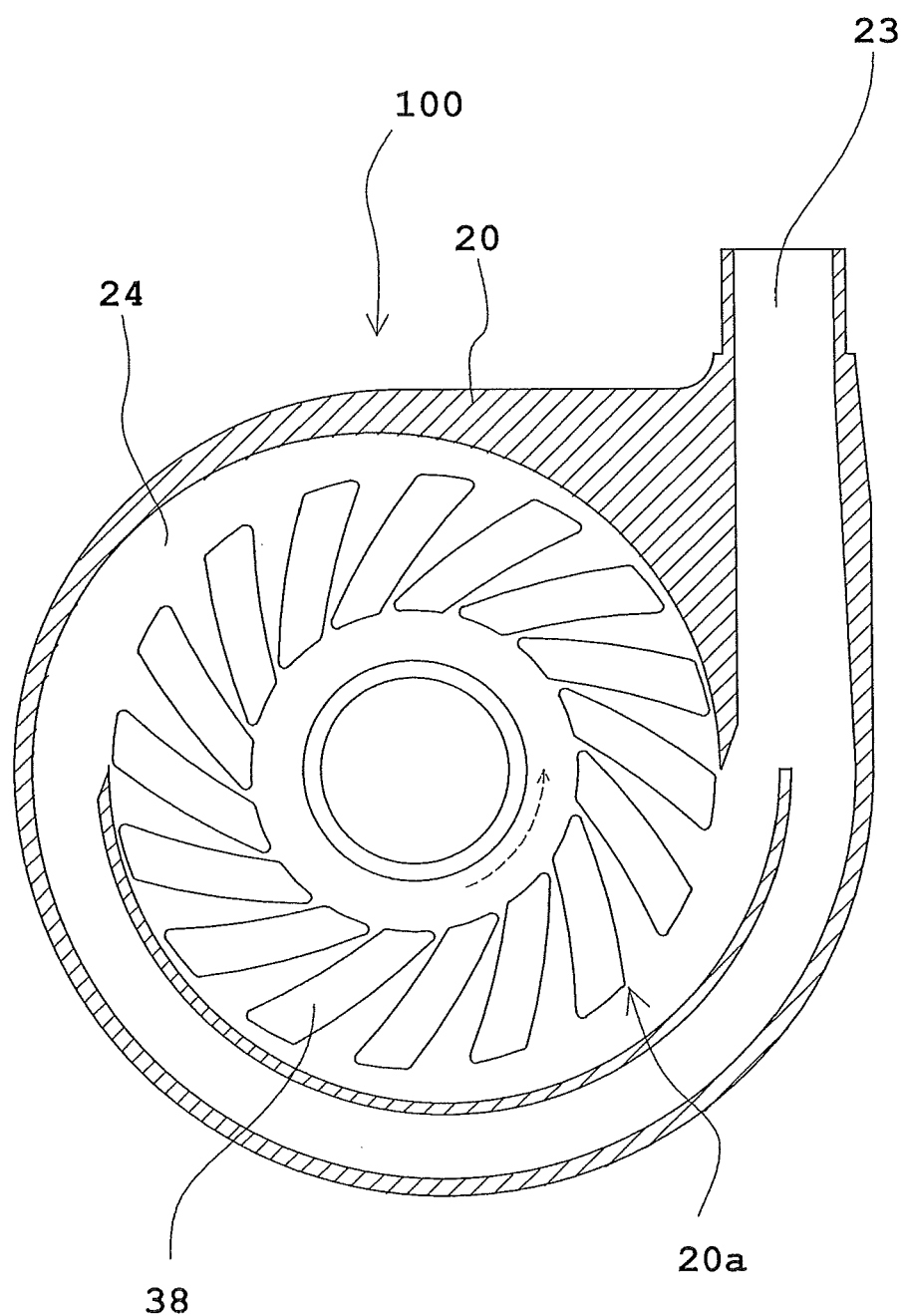
FIG. 21 is a sectional view showing a state in which an impeller is removed from the sectional view taken along a line D-D in FIG. 19.
Figure 22:
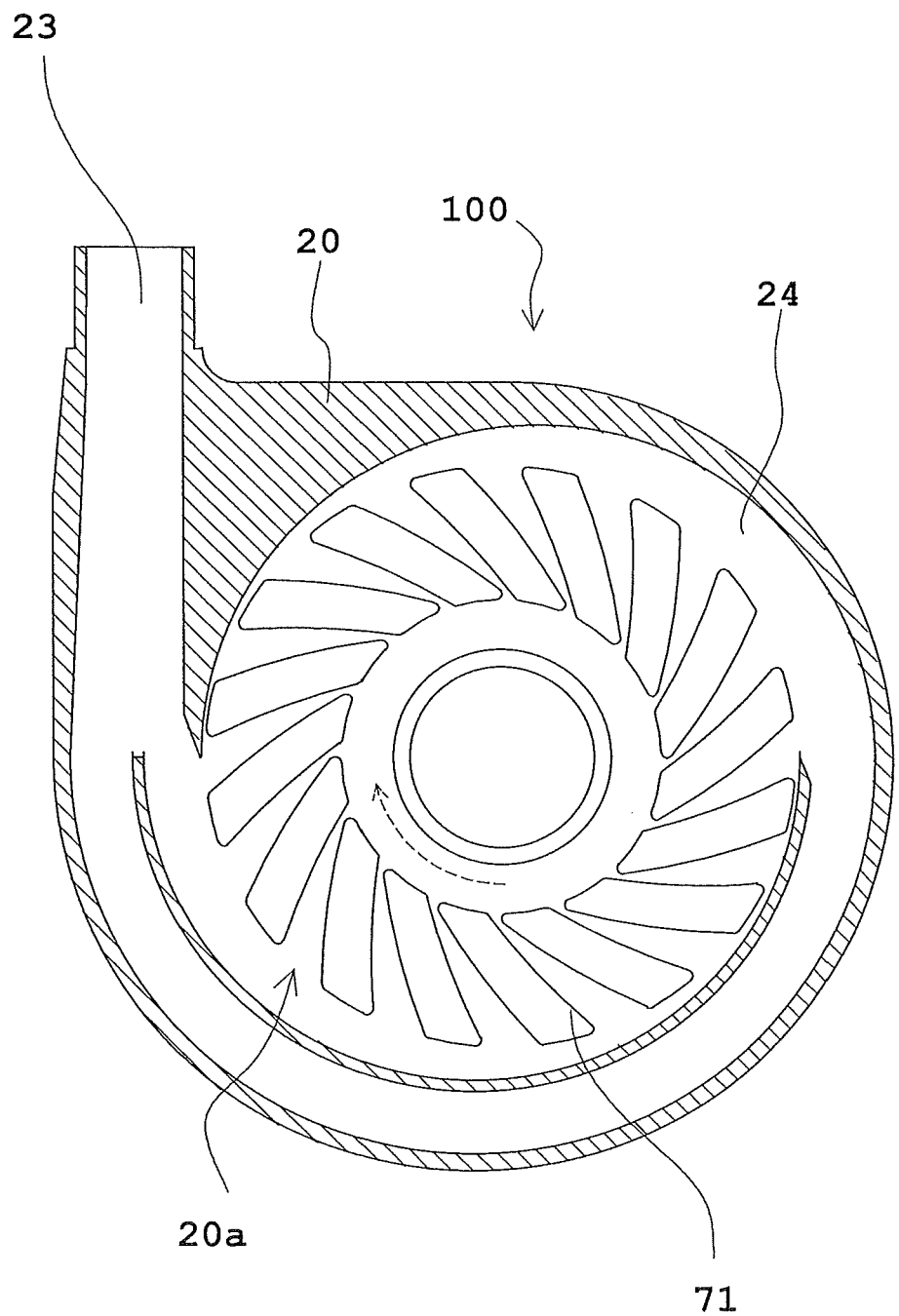
FIG. 22 is a sectional view showing a state in which an impeller is removed from the sectional view taken along a line E-E in FIG. 19.

FIG. 16 is a block diagram of an embodiment including a control mechanism of a blood pump apparatus of the present invention. FIG. 17 is a front view showing a blood pump apparatus according to still another embodiment of the present invention. FIG. 18 is a plan view showing the blood pump apparatus shown in FIG. 17. FIG. 19 is a sectional view taken along a line C-C in FIG. 18. FIG. 20 is a sectional view taken along a line D-D in FIG. 19. FIG. 21 is a sectional view showing a state in which an impeller is removed from the sectional view taken along a line D-D in FIG. 19. FIG. 22 is a sectional view showing a state in which an impeller is removed from the sectional view taken along a line E-E in FIG. 19.

A blood pump apparatus 100 of the present invention includes a housing 20 having a blood inlet port 22 and a blood outlet port 23; a pump section 2 including an impeller 21 having a magnetic material 25 disposed therein and rotating in the housing 20 to feed blood; and an impeller rotational torque generation section 3 for attracting thereto the impeller 21 of the pump section 2 and rotating the impeller 21. The pump section 2 further includes a first groove 38 for hydrodynamic bearing provided on an inner surface of the housing 20 at the side of the impeller rotational torque generation section 3 or a surface of the impeller 21 at the side of the impeller rotational torque generation section 3. The impeller 21 rotates without contacting the housing 20. The pump section 2 has a sensor 45 having a function of measuring the position of the impeller 21 when the impeller 21 is rotated without contacting the housing 20 by a hydrodynamic pressure generated by the hydrodynamic bearing groove 38.

Therefore in the blood pump apparatus of this embodiment, the impeller is rotated without contacting the housing 20 by utilizing the hydrodynamic bearing groove, and the position of the impeller can be checked.

As shown in FIGS. 17 through 22, the blood pump apparatus 100 of this embodiment is a centrifugal blood pump apparatus and has the housing 20 having the blood inlet port 22 and the blood outlet port 23, the centrifugal pump section 2 having the impeller 21 rotating inside the housing 20 to feed blood by a centrifugal force generated during its rotation, and the impeller rotational torque generation section 3 for the impeller 21.

The blood pump apparatus of the embodiment of the present invention is not limited to the above-described centrifugal pump apparatus. For example, the blood pump apparatus may be of an axial-flow type or of a diagonal-flow type.

In the centrifugal blood pump apparatus 100 of this embodiment, the impeller rotational torque generation section 3 has a rotor 31 having a magnet 33 for attracting thereto a magnetic material 25 of the impeller 21 and a motor 34 for rotating the rotor 31.

As shown in FIG. 19, the impeller 21 rotates without contacting the inner surface of the housing 20 by a pressure generated by the hydrodynamic bearing groove when the impeller 21 rotates.

The housing 20 has the blood inlet port 22 and the blood outlet port 23 and is formed of a non-magnetic material. The housing 20 accommodates a blood chamber 24 communicating with the blood inlet and outlet ports 22 and 23. The housing 20 also accommodates the impeller 21 therein. The blood inlet port 22 projects substantially vertically from the vicinity of the center of the upper surface of the housing 20. The blood inlet port 22 does not necessarily have to be formed as a straight pipe, but may be formed as a curved pipe or a bent pipe. As shown in FIGS. 18, 20, 21, and 22, the blood outlet port 23 projects tangentially from a side surface of the approximately cylindrical housing 20.

As shown in FIG. 19, the disc-shaped impeller 21 having a through-hole in the center thereof is accommodated inside the blood chamber 24 formed inside the housing 20. As shown in FIGS. 18 and 19, the impeller 21 includes an annular plate-shaped member (lower shroud) 27 forming the lower surface thereof, an annular plate-shaped member (upper shroud) 28 forming the upper surface thereof and opening at the center thereof, and a plurality of (for example, seven) vanes 18 formed between the lower shroud 27 and the upper shroud 28. A plurality (for example, seven) of blood passages 26 partitioned from one another by the adjacent vanes 18 is formed between the lower shroud 27 and the upper shroud 28. As shown in FIG. 19, each of the blood passages 26 communicates with the center opening of the impeller 21 and extends from the center opening of the impeller 21 to its periphery, with each of the blood passages 26 becoming gradually larger in the width thereof. In other words, each vane 18 is formed between the adjacent blood passages 26. In the embodiment, the vanes 18 and blood passages 26 are spaced at equiangular intervals respectively and formed in substantially the same shape respectively.

As shown in FIGS. 19 and 20, a plurality (for example, 10 to 40) of the magnetic materials 25 (for example permanent magnet, follower magnet) are embedded in the impeller 21. In the embodiment, the magnetic materials 25 are embedded in the lower shroud 27. A permanent magnet 33, to be described later, provided in the rotor 31 of the rotational torque generation section 3 attracts the magnetic material 25 embedded in the impeller toward the side opposite to the side where the blood inlet port 22 is disposed. In this operation, the magnetic material 25 serves as a means for allowing the impeller 21 and the rotor 31 to be magnetically coupled to each other and transmitting the rotational torque from the rotational torque generation section 3 to the impeller 21.

The magnetic coupling, to be described later, between the impeller 21 and the rotor 31 is ensured by embedding a plurality of the magnetic materials 25 (permanent magnet) in the impeller 21. It is preferable that each of the magnetic materials 25 is circular.

As shown in FIG. 19, included in the rotational torque generation section 3 are the rotor 31 accommodated in the housing 20 and a motor 34 for rotating the rotor 31. The rotor 31 has a plurality of permanent magnets 33 disposed on a surface thereof at the side of the centrifugal pump section 2. The center of the rotor 31 is fixedly secured to the rotational shaft of the motor 34. A plurality of the permanent magnets 33 is equiangularly distributed in accordance with the arrangement mode (number and position) of the permanent magnets 25 of the impeller 21.

In the coupling between the permanent magnet of the impeller and that of the motor, it is preferable to dispose the permanent magnet in such a way that an attractive force is generated between the impeller and the motor even though they are uncoupled from each other by an external force and a power swing occurs therebetween. Thereby even though the impeller and the motor are uncoupled from each other and the power swing occurs therebetween, they can be coupled to each other easily again because the attractive force is present therebetween.

As shown in FIGS. 18 and 19, in this embodiment, the impeller 21 has a plurality of a ring-shaped permanent magnet 29. In the embodiment, the permanent magnet 29 is embedded in the upper shroud 28. A second permanent magnet 41 attracts the permanent magnet 29 embedded in the impeller toward the side opposite to the side where the impeller rotational torque generation section 3 (namely, rotor) is disposed. The permanent magnet 29 is so disposed that an attractive force is generated between the permanent magnet 29 and the second permanent magnet 41. The permanent magnet 29 may be plural (for example, 10 to 40) provided.

As shown in FIG. 21, in the centrifugal blood pump apparatus 100 of the embodiment, the housing 20 accommodates the impeller 21 and has the first groove 38 for hydrodynamic bearing formed on a rotor-side inner surface 20a of the housing 20 forming the blood chamber 24. A hydrodynamic bearing effect generated between the first groove 38 for hydrodynamic bearing and the impeller 21 by a rotation of the impeller 21 at a speed more than a predetermined number of rotations allows the impeller 21 to rotate without contacting the inner surface of the housing 20.

As shown in FIGS. 18 and 19, the centrifugal pump section 2 has at least one fixed permanent magnet 41 for attracting thereto the magnetic material 29 (embedded in upper shroud 28) of the impeller 21 provided separately from the magnetic material 25 of the impeller 21. More specifically, as shown with broken lines in FIG. 18, the circular arc-shaped permanent magnet 41 is plural used. The impeller 21 is attracted to opposite directions by the permanent magnet 33 of the rotor 31 and the permanent magnet 41. The permanent magnets 41 are provided at equiangular intervals around the axis of the impeller 21. It is possible to use not less than three permanent magnets 41, for example, four permanent magnets 41.

The blood pump section 2 has a sensor 45 having a function of measuring the position of the impeller 21. More specifically, the blood pump section 2 has a plurality of position sensors 45 accommodated in the housing 20. The position sensors (three) 45 are spaced at equiangular intervals around the axis of the impeller 21. The electromagnets 41 are also spaced at equiangular intervals around the axis of the impeller 21. By providing the three position sensors 45, it is possible to measure the inclination of the impeller 21 in the direction of the rotational axis (z-axis) and in the direction of an x-axis and a y-axis orthogonal to the rotational axis (z-axis). The position sensors 45 detect the gap between them and the magnetic material 29. As shown in FIG. 16, outputs of the position sensors 45 are transmitted to a control part 51 of the control unit 6 controlling motor current.

The control unit 6 has a sensor unit 57 for the sensors 45, the control part 51, a power amplifier 52 for the motor, a motor control circuit 53, and a motor current monitoring part 55.

It is preferable that the blood pump apparatus has a blood viscosity-computing function of computing a blood viscosity by using the output of the position sensor 45. More specifically, the control unit 6 has a viscosity-measuring function. The blood viscosity-computing function includes a function of temporarily decreasing the number of rotations of the impeller to a predetermined number of rotations; and a function of detecting a vertical swivel length of the impeller by using the output of the sensor when the number of rotations of the impeller has decreased to the predetermined number of rotations by the function of temporarily decreasing the number of rotations and computing the blood viscosity by using the detected vertical swivel length. It is preferable that the blood viscosity-computing function has a storing part for storing data of the relationship between the vertical swivel length of the impeller and the blood viscosity at the predetermined number of rotations of the impeller or a viscosity-computing equation obtained from the data of the relationship and a viscosity-computing function for computing the blood viscosity from data of the vertical swivel length obtained by the output of the sensor and the data of the relationship between the vertical swivel length of the impeller and the blood viscosity stored by the storing part or the viscosity-computing equation.

More specifically, in the blood pump apparatus 100 of this embodiment, the control unit 6 has the function of temporarily decreasing the number of rotations of the motor to a predetermined number of rotations by adjusting motor current, stores relation data for various blood viscosities between vertical swivel movements (indicated by μm peak to peak in vertical swivel movement of the impeller) of the impeller at predetermined number of rotations of the motor and blood viscosity, and has the function of computing the blood viscosity from results detected by the sensor and the number of rotations of the motor.

With reference to FIG. 18, when the distance between the position sensor and the impeller is detected by the position sensor 45 spaced at 120 degrees, the output of the position sensor 45 fluctuates like a sine wave in a period (for example, 0.05 seconds at 1200 rpm) of the number of rotations of the motor. The peak to peak of the sine wave indicates the vertical swivel of the impeller. The vertical swivel is as shown in table 1 when the centrifugal hydrodynamic bearing pump has the impeller having a diameter of 40 mm.

The state of the blood outlet port is shown in conditions of "Open" and "Close" normally used for a pump. The higher the viscosity, the smaller the vertical swivel when the impeller rotates at a small number of rotations (1000 rpm) at which the hydrodynamic pressure effect is not displayed at the blood inlet port. On the other hand, at 1500 rpm, the vertical swivel length is reduced by the display of the hydrodynamic pressure effect at the blood inlet port. This relationship is measured in advance for a plurality of viscosities (for example, intervals of 1 mPa·s at 2 to 5 mPa·s) at predetermined number of rotations (for example, 800 to 1200 rpm) of the impeller, and in addition, data of results of the measurement or relational expression data obtained from the data of results of the measurement is stored. Thereafter the viscosity of the blood is computed from a measured value of the vertical swivel and the above-described data. The vertical swivel varies to some extent in dependence on the state of the blood outlet port. When the blood pump apparatus is used as an auxiliary artificial heart of an organism, a state close to "Open" or "Close" can be found from a change in the motor current. The vertical swivel at that time is selected.

TABLE 1

| Outlet port | Open | Open | Close | Close |
|---|---|---|---|---|
| Viscosity | 2 mPa·s | 4 mPa·s | 2 mPa·s | 4 mPa·s |
| 1000 rpm | 20 | 18 | 25 | 18 |
| 1500 rpm | 25 | 25 | 27 | 28 |

The pump apparatus 100 of the present invention has the first groove 38 for hydrodynamic bearing provided on an inner surface of the housing 20 at the side of the impeller rotational torque generation section 3 thereof or a surface of the impeller 21 at the side of the impeller rotational torque generation section 3 thereof.

As shown in FIG. 21, the first groove 38 for hydrodynamic bearing has a size corresponding to that of the bottom surface (surface at rotor side) of the impeller 21. As shown in FIG. 6, the first groove 38 for hydrodynamic bearing extends spirally (in other words, curved) outwardly to the vicinity of the outer edge of the inner surface 20a, with one end of the first groove 38 for hydrodynamic bearing disposed on the periphery (circumference) of a circle spaced outward at a short distance from the center of the inner surface 20a of the housing 20 and with the width thereof becoming outwardly gradually larger. The first groove 38 for hydrodynamic bearing is composed of a group of a large number of grooves for hydrodynamic bearing. The first grooves 38 have substantially the same configuration and are spaced at almost equal intervals. Each of the first grooves 38 for hydrodynamic bearing is concavely formed. It is preferable that the depth thereof is in the range of 0.05 to 0.4 mm. The number of the first grooves 38 for hydrodynamic bearing is favorably in the range of 6 to 36. In the embodiment, 16 grooves for hydrodynamic bearing are provided at equiangular intervals around the axis of the impeller 21.

The groove for hydrodynamic bearing may be disposed on the rotor-side surface of the impeller 21 instead of disposing it at the housing side. It is preferable that the groove for hydrodynamic bearing disposed on the rotor-side surface of the impeller 21 has the same construction as that of the groove for hydrodynamic bearing disposed at the housing side.

The first groove 38 for hydrodynamic bearing is attracted toward the impeller torque generation section 3. Owing to the hydrodynamic bearing effect generated between the first groove 38 for hydrodynamic bearing disposed on the housing and the bottom surface of the impeller 21 (or between the first groove 38 for hydrodynamic bearing disposed on the impeller and the inner surface of the housing), the impeller 21 rotates without contacting the inner surface of the housing 20 with the impeller 21 levitating slightly from the inner surface of the housing 20, thus providing a blood passage between the lower surface of the impeller 21 and the inner surface of the housing 20. Thereby it is possible to prevent blood from staying therebetween and thrombus from occurring because the blood is prevented from staying therebetween.

In pump apparatus of the present invention, as shown in FIGS. 20 and 6, each hydrodynamic bearing groove 38 has a first side 38a and a second side 38b both extending from the periphery of the portion 39 thereof in which a hydrodynamic bearing groove is formed toward the central side thereof and opposed to each other, a third side 38c connecting one end of the first side 38a and one end of the second side 38b to each other, and a fourth side 38d connecting the other end of the first side 38a and the other end of the second side 38b to each other. The first side 38a and the second side 38b are formed as a circular arc respectively in such a way that the centers of the circular arcs are different from each other.

In this embodiment, the first side 38a and the second side 38b are composed of a circular arc respectively in such a way that the circular arcs have different centers and radii. Instead, the hydrodynamic bearing groove may be composed of circular arcs having the same center and different radii or different centers and the same radius. But the hydrodynamic bearing groove composed of circular arcs having different centers and radii can be provided with a larger width in the peripheral portion of the portion in which a hydrodynamic bearing groove is formed thereof than the hydrodynamic bearing groove composed of circular arcs having the same center and different radii or the hydrodynamic bearing groove composed of different centers and the same radius.

In this embodiment, the third side 38c and the fourth side 38d are formed as a circular arc respectively in such a way that the circular arcs have the same center and different radii.

With reference to FIG. 6, the first side 38a is formed as the circular arc having a radius Ra and a center disposed at a point P2 located outside the portion 39 in which a hydrodynamic bearing groove is formed. The second side 38b is formed as the circular arc having a radius Rb and a center disposed at a point P3 located outside the portion 39 in which a hydrodynamic bearing groove is formed. Although the radius Ra varies according to the size of the blood pump apparatus, the radius Ra is set to preferably in the range of 30 to 70 mm. Although the radius Rb varies according to the size of the blood pump apparatus, the radius Rb is set to preferably in the range of 30 to 70 mm. It is preferable that the distance between the points P2 and P3 is set to the range of 3 to 10 mm. The third side 38c is formed as the circular arc having a radius Rc and a center disposed at a center P1 of the portion 39 in which a hydrodynamic bearing groove is formed. The fourth side 38d is formed as the circular arc having a radius Rd and a center disposed at the center P1 of the portion 39 in which a hydrodynamic bearing groove is formed. Although the radius Rc varies according to the size of the blood pump apparatus, the radius Rc is set to preferably in the range of 6 to 18 mm. Although the radius Rd varies according to the size of the blood pump apparatus, the radius Rd is set to preferably in the range of 15 to 30 mm. It is preferable that the radius Rc is 0.3 to 0.8 times the radius Rd.

As shown in FIG. 6, the value relating to a groove width ratio s ($s=B_0/B$) computed from the width $B_0$ of the peripheral portion of each hydrodynamic bearing groove and the sum B ($B=B_0-B1$) of the width $B_0$ and the width B1 of the hydrodynamic bearing groove-non-present portion between the peripheral portions of the adjacent grooves for hydrodynamic bearing is in a range of 0.6 to 0.8.

As shown in FIG. 7, in the pump apparatus of this embodiment, the hydrodynamic bearing groove 38 composed of the four sides 38a, 38b, 38c, and 38d, four corners 38e, 38f, 38g, and 38h are rounded. It is preferable that the four corners are rounded at not less than 0.1 mm.

With reference to FIG. 8, the value relating to a groove depth ratio a ($a=h1/h2$) computed from the distance h1 between the impeller 21 and the housing 20 in the hydrodynamic bearing groove of the portion in which a hydrodynamic bearing groove is formed during the rotation of the impeller 21 and from the distance h2 between the impeller 21 and the housing 20 in the hydrodynamic bearing groove-non-present portion of the portion in which a hydrodynamic bearing groove is formed during the rotation of the impeller 21 is in the range of 1.5 to 2.5.

As described above, since the hydrodynamic bearing groove 38 is so constructed that the value relating to a groove width ratio s ($s=B_0/B$) is in the range of 0.6 to 0.8 and that the value relating to a groove depth ratio a ($a=h1/h2$) is in the range of 1.5 to 2.5, the hydrodynamic bearing groove 38 is wider and shallower than a logarithmic groove for hydrodynamic bearing having the same number of grooves. Thus the hydrodynamic bearing groove 38 generates a less amount of hemolysis.

As shown in FIG. 22, a second groove 71 for hydrodynamic bearing has a size corresponding to that of the upper surface (surface at permanent magnet side) of the impeller 21. As shown in FIG. 6, the second groove 71 for hydrodynamic bearing extends spirally (in other words, curved) outwardly to the vicinity of the outer edge of the inner surface 20a, with one end of the second groove 71 for hydrodynamic bearing disposed on the periphery (circumference) of a circle spaced outward at a short distance from the center of the inner surface 20a of the housing 20 and with the width thereof becoming outwardly gradually larger. A plurality of the grooves 71 for hydrodynamic bearing has substantially the same configuration and is spaced at almost equal intervals. Each of the second groove 71 for hydrodynamic bearing is concavely formed. It is preferable that the depth thereof is in the range of 0.05 to 0.4 mm. The number of the second groove 71 for hydrodynamic bearing is favorably in the range of 6 to 36. In the embodiment, 16 grooves for hydrodynamic bearing are provided at equiangular intervals around the axis of the impeller 21.

The groove for hydrodynamic bearing may be disposed on the permanent magnet-side surface of the impeller 21 instead of disposing it at the housing side. It is preferable that the groove for hydrodynamic bearing disposed on the permanent magnet-side surface of the impeller 21 has the same construction as that of the groove for hydrodynamic bearing disposed at the housing side.

The blood pump apparatus 100 has the second hydrodynamic bearing groove 71. Thereby even though the impeller is proximate to a portion of the housing at the side of the second hydrodynamic bearing groove 71 when an excessive hydrodynamic pressure is generated by a disturbance or by the first hydrodynamic bearing groove, it is possible to prevent the impeller from contacting the portion of the housing at the side of the second hydrodynamic bearing groove 71 because a hydrodynamic pressure is generated by the second hydrodynamic bearing groove.

In the embodiment, as shown in FIGS. 21, 6, and 7, similarly to the hydrodynamic bearing groove 38, each hydrodynamic bearing groove 71 has a first side 38a and a second side 38b both extending from the periphery of the portion 39 thereof in which a hydrodynamic bearing groove is formed toward the central side thereof and opposed to each other, a third side 38c connecting one end of the first side 38a and one end of the second side 38b to each other, and a fourth side 38d connecting the other end of the first side 38a and the other end of the second side 38b to each other. The first side 38a and the second side 38b are formed as a circular arc respectively in such a way that the centers of the circular arcs are different from each other. In this embodiment, the first side 38a and the second side 38b are composed of a circular arc respectively in such a way that the circular arcs have different centers and radii. In this embodiment, the third side 38c and the fourth side 38d are formed as a circular arc respectively in such a way that the circular arcs have the same center and different radii.

In the pump apparatus of the present invention, as shown in FIG. 8, the value relating to a groove depth ratio a ($a=h1/h2$) computed from the distance h1 between the impeller 21 and the housing 20 in the hydrodynamic bearing groove of the portion in which a hydrodynamic bearing groove is formed during the rotation of the impeller 21 and from the distance h2 between the impeller 21 and the housing 20 in the hydrodynamic bearing groove-non-present portion of the portion in which a hydrodynamic bearing groove is formed during the rotation of the impeller 21 is in the range of 1.5 to 2.5.

As described above, since the hydrodynamic bearing groove 71 is so constructed that the value relating to a groove width ratio s ($s=B_0/B$) is in the range of 0.6 to 0.8 and that the value relating to a groove depth ratio a ($a=h1/h2$) is in the range of 1.5 to 2.5, the hydrodynamic bearing groove 71 is wider and shallower than a logarithmic groove for hydrodynamic bearing having the same number of grooves. Thus the hydrodynamic bearing groove 38 generates a less amount of hemolysis.

A centrifugal blood pump apparatus according to another embodiment of the present invention is described below.

Figure 23:
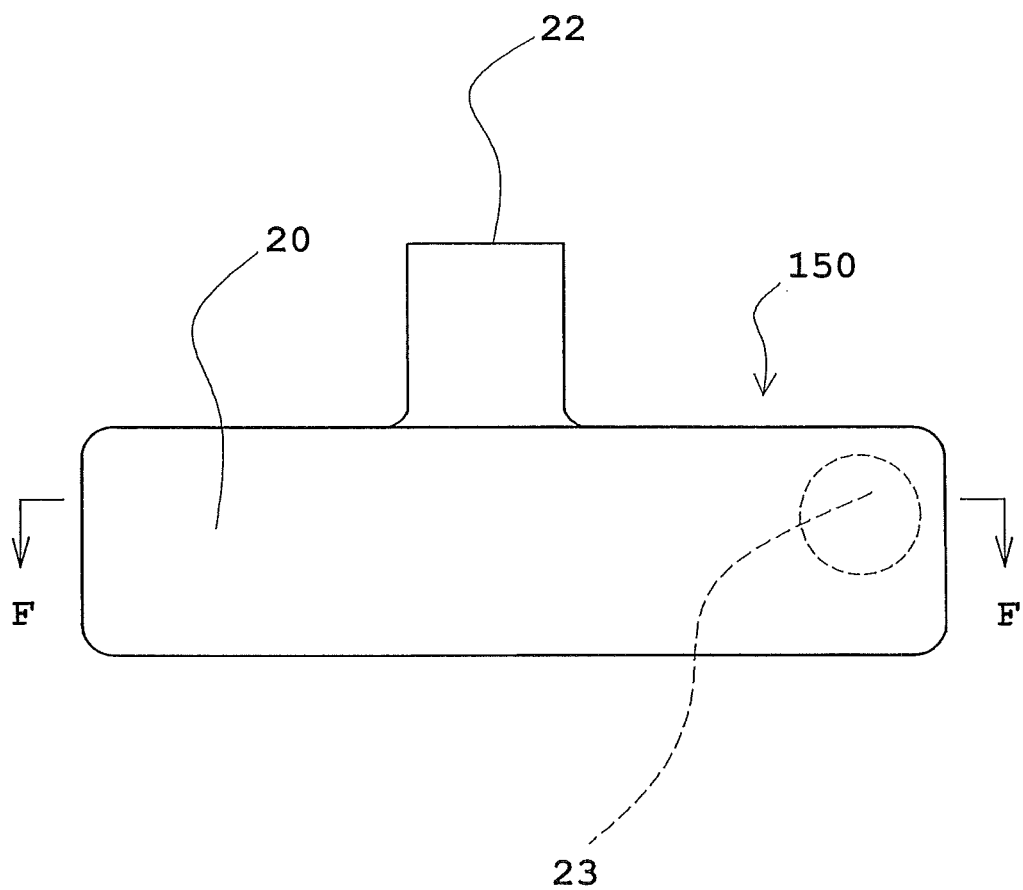
FIG. 23 is a front view showing a blood pump apparatus according to another embodiment of the present invention.
Figure 24:
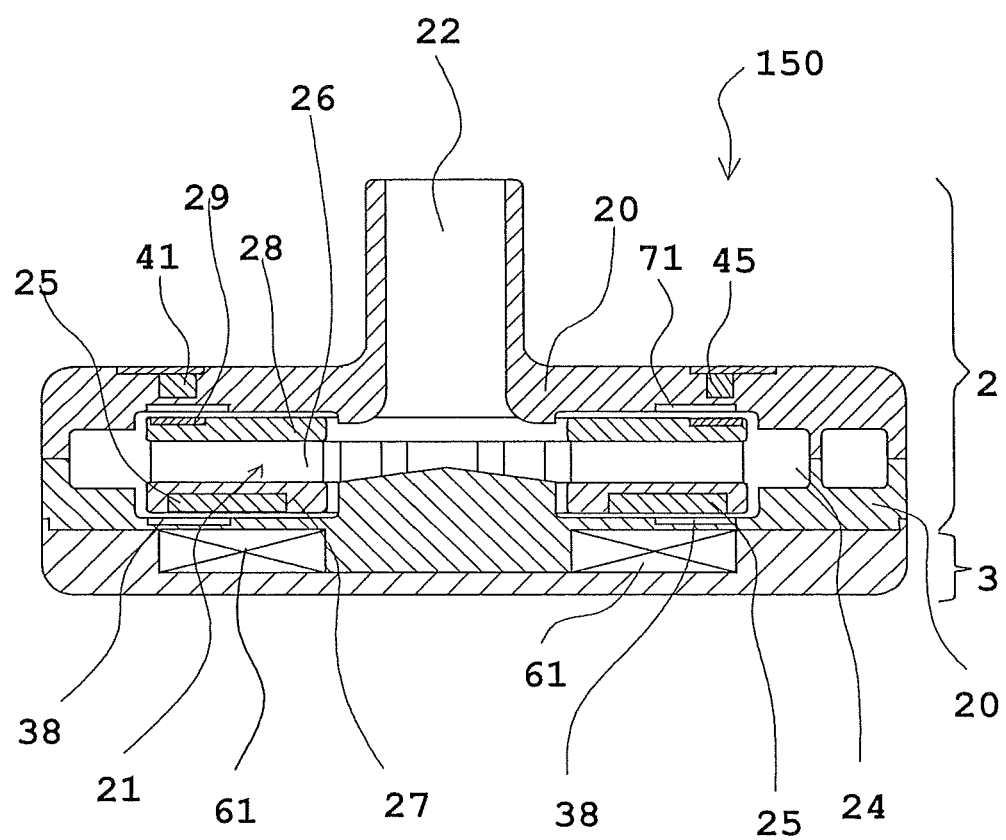
FIG. 24 is a vertical sectional view showing the blood pump apparatus shown in FIG. 23.
Figure 25:
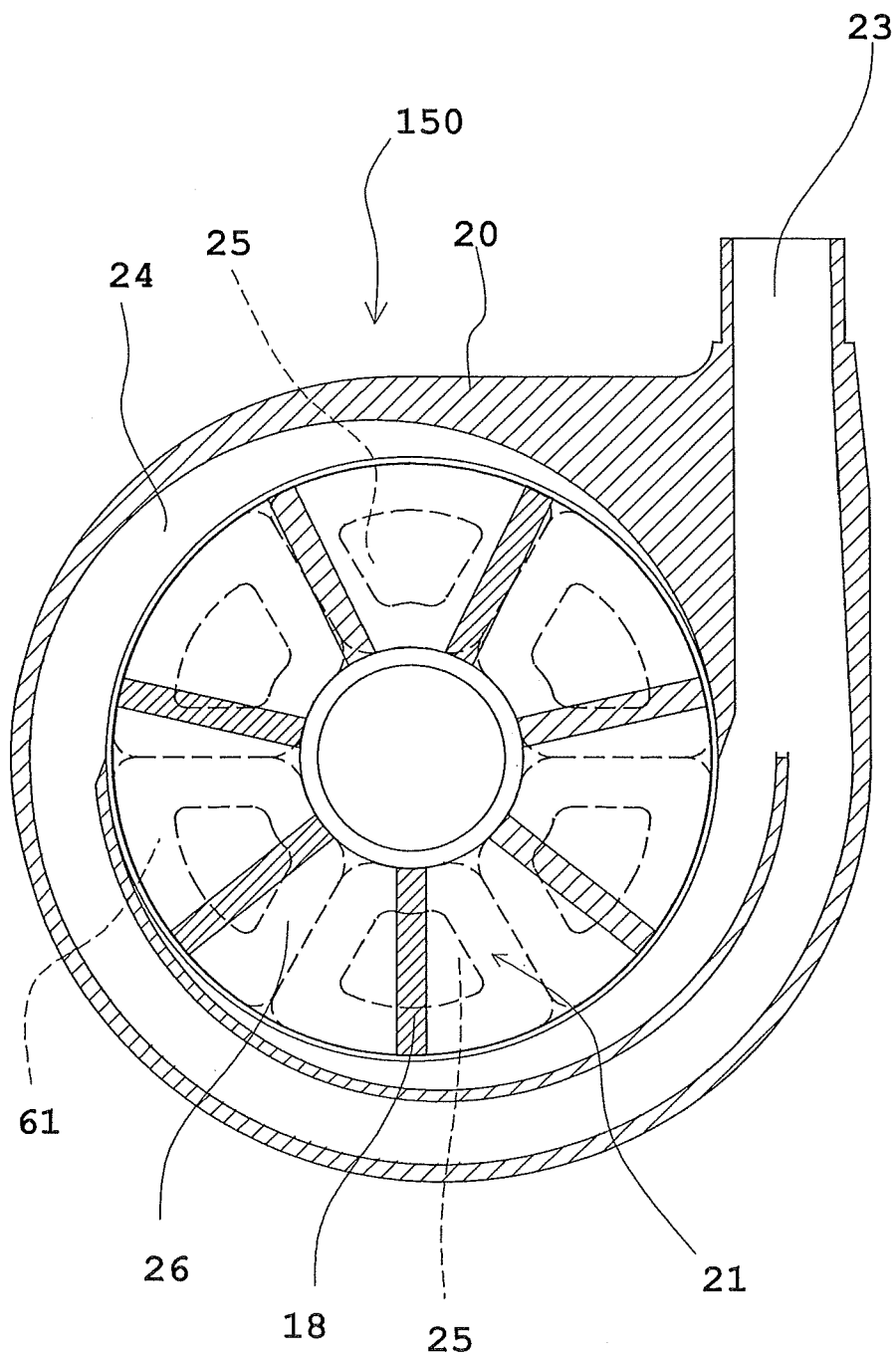
FIG. 25 is a sectional view, taken along a line F-F in FIG. 23, showing the centrifugal blood pump apparatus.
Figure 26:
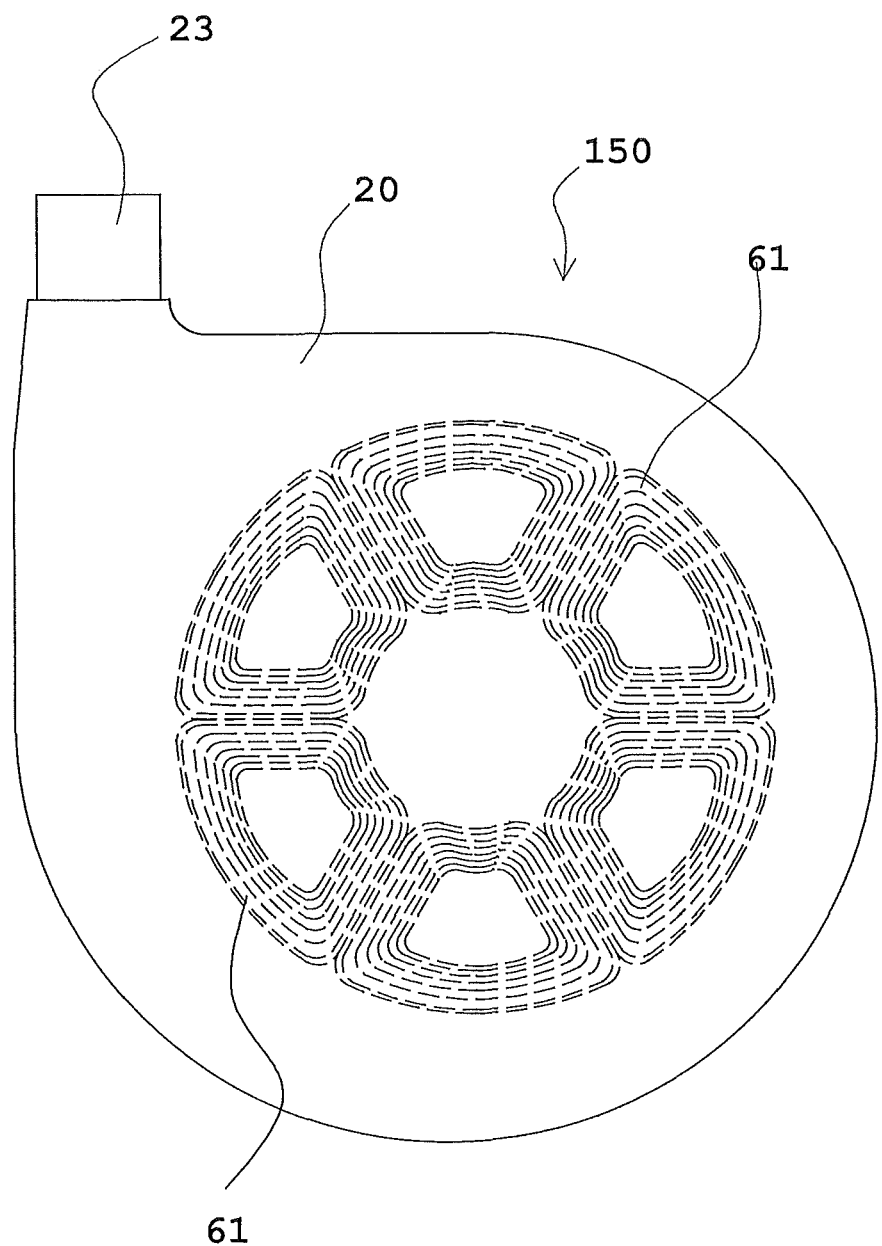
FIG. 26 is a bottom view showing the centrifugal blood pump apparatus shown in FIG. 23.

FIG. 23 is a front view showing a blood pump apparatus according to another embodiment of the present invention. FIG. 24 is a vertical sectional view showing the blood pump apparatus shown in FIG. 23. FIG. 25 is a sectional view, taken along a line F-F in FIG. 23, showing the centrifugal blood pump apparatus. FIG. 26 is a bottom view showing the centrifugal blood pump apparatus shown in FIG. 23. A plan view of the centrifugal blood pump apparatus according to the embodiment shown in FIG. 23 is the same as the plan view shown in FIG. 18.

A pump apparatus 150 of this embodiment is different from the pump apparatus 100 of the above-described embodiment in only the mechanism of the impeller rotational torque generation section 3. The impeller rotational torque generation section 3 of the pump apparatus 150 does not have a rotor, but is of a type of driving the impeller directly. In the pump apparatus 150 of this embodiment, the impeller 21 rotates without contacting the inner surface of the housing 20 by a pressure generated by the hydrodynamic bearing groove 38 when the impeller 21 rotates. In description which is described below, constructions different from those of the above-described embodiments are described. The mode of each of a sensor 45, grooves 38, 71 for hydrodynamic bearing, the control unit 6 is the same as that of the above-described embodiments.

As shown in FIGS. 24 and 26, the impeller rotational torque generation section 3 of the pump apparatus 150 has a plurality of stator coils 61 accommodated in the housing 20. The stator coils 61 are disposed along a circumference at equiangular intervals around the axis thereof. More specifically, six stator coils 61 are used. Multilayer stator coils are used as the stator coils 61. A rotating magnetic field is generated by switching the direction current flowing through each stator coil 61. The impeller is attracted to the rotor by the rotating magnetic field and rotates.

As shown in FIG. 25, a plurality (for example, 6 to 12) of the magnetic materials 25 (for example, permanent magnet, follower magnet) is embedded in the impeller 21. In the embodiment, the magnetic, materials 25 are embedded in the lower shroud 27. The stator coils 61 provided in the rotational torque generation section 3 attracts the magnetic material 25 embedded in the impeller toward the side opposite to the side where the blood inlet port 22 is disposed. In this operation, the magnetic materials 25 couple to the operation of the stator coils 61 and transmit the rotational torque from the rotational torque generation section 3 to the impeller 21.

The magnetic coupling, to be described later, between the impeller 21 and the stator rotor 61 is ensured by embedding a plurality of the magnetic materials 25 (permanent magnet) in the impeller 21. It is preferable that each of the magnetic materials is approximately trapezoidal. The magnetic materials 25 are ring-shaped or plate-shaped. It is preferable that the number and arrangement mode of the magnetic materials 25 correspond to those of the stator coils 61. The magnetic materials 25 are disposed circumferentially at equiangular intervals around the axis of the impeller in such a way that positive and negative poles thereof alternate with each other.

In the centrifugal blood pump apparatus of the embodiment, the above-described peripheral configuration of the hydrodynamic bearing groove is not limited to the above-described one. For example, it is possible to adopt the logarithmic spiral groove as shown in FIG. 15.

What is claimed is:

1. A blood pump apparatus comprising:
   a housing having a blood inlet port and a blood outlet port;
   a pump section including an impeller having a magnetic material and rotating in said housing to feed blood; and
   an impeller rotational torque generation section for attracting thereto said impeller of said pump section and rotating said impeller,
   wherein said pump section further comprises a first groove for hydrodynamic bearing provided on an inner surface of said housing at a side of said impeller rotational torque generation section,
   wherein said impeller includes both a ring-shaped permanent magnet and said magnetic material and said impeller is rotated without contacting said housing,
   wherein said housing includes a permanent magnet attracting said ring-shaped permanent magnet of said impeller in a direction opposite to a direction in which said impeller is attracted by said impeller rotational torque generation section,
   wherein a second groove for hydrodynamic bearing is provided on a permanent magnet-side inner surface of said housing, and said impeller is devoid of any grooves for hydrodynamic bearing, and
   wherein said impeller rotational torque generation section has a plurality of stator coils, disposed circumferentially, for attracting thereto said magnetic material of said impeller and rotating said impeller.

2. A blood pump apparatus according to claim 1, wherein a plurality of grooves for hydrodynamic bearing is formed on said portion in which a groove for hydrodynamic bearing is formed;
   each of said grooves for hydrodynamic bearing has a first side and a second side both extending from a periphery of said portion in which a groove for hydrodynamic bearing is formed toward a central side thereof and opposed to each other, a third side connecting one end of said first side and one end of said second side to each other, and a fourth side connecting said other end of said first side and said other end of said second side to each other;
   said first side and said second side are formed as a circular arc respectively in such a way that centers of said circular arcs are different from each other;
   a value relating to a groove depth ratio a ($a=h1/h2$) computed from a distance h1 between said impeller and said housing in said groove for hydrodynamic bearing of said portion in which a groove for hydrodynamic bearing is formed during a rotation of said impeller and from a distance h2 between said impeller and said housing in a groove for hydrodynamic bearing-non-present portion of said portion in which a groove for hydrodynamic bearing is formed during said rotation of said impeller is in a range of 1.5 to 2.5; and
   a value relating to a groove width ratio s ($s=B_0/B$) computed from a width $B_0$ of a peripheral portion of each groove for hydrodynamic bearing and a sum B ($B=B_0+$ B1) of said width $B_0$ and a width B1 of a hydrodynamic bearing groove-non-present portion between peripheral portions of adjacent grooves for hydrodynamic bearing is in a range of 0.6 to 0.8.

3. A centrifugal blood pump apparatus according to claim 2, wherein said four corners of said groove for hydrodynamic bearing are rounded.

4. A centrifugal blood pump apparatus according to claim 2, wherein a plurality of grooves for hydrodynamic bearing is formed on said portion in which a groove for hydrodynamic bearing is formed;
   each of said grooves for hydrodynamic bearing has a first side and a second side both extending from a periphery of said portion in which a groove for hydrodynamic bearing is formed toward a central side thereof and opposed to each other, a third side connecting one end of said first side and one end of said second side to each other, and a fourth side connecting said other end of said first side and said other end of said second side to each other;
   said first side and said second side are formed as a circular arc respectively in such a way that centers of said circular arcs are different from each other; and
   four corners composed of said four sides are rounded.

5. A centrifugal blood pump apparatus according to claim 4, wherein said third side and said fourth side are formed as a circular arc respectively in such a way that said circular arcs have a same center and different radii.

6. A centrifugal blood pump apparatus according to claim 1, wherein said impeller has an upper shroud and a lower shroud, and said ring-shaped permanent magnet is embedded in the upper shroud.

7. A blood pump apparatus comprising:
   a housing having a blood inlet port and a blood outlet port;
   a pump section including an impeller having both a magnetic material and a ring-shaped permanent magnet and rotating in said housing to feed blood; and
   an impeller rotational torque generation section for attracting thereto said impeller of said pump section and rotating said impeller,
   wherein said pump section further comprises a first groove for hydrodynamic bearing provided on an inner surface of said housing at a side of said impeller rotational torque generation section or a surface of said impeller at said side of said impeller rotational torque generation section,
   wherein said impeller is rotated without contacting said housing,
   wherein said housing includes a permanent magnet attracting said magnetic material of said impeller or the ring-shaped permanent of said impeller in a direction opposite to a direction in which said impeller is attracted by said impeller rotational torque generation section,
   wherein a second groove for hydrodynamic bearing is provided on a permanent magnet-side inner surface of said housing or said permanent magnet-side surface of said impeller, and
   wherein said impeller rotational torque generation section has a plurality of stator coils, disposed circumferentially, for attracting thereto said magnetic material of said impeller and rotating said impeller,
   wherein said first groove for hydrodynamic bearing comprises a plurality of grooves for hydrodynamic bearing,
   each of said plurality of grooves for hydrodynamic bearing has a first side and a second side both extending from a periphery of said portion in which a groove for hydrodynamic bearing is formed toward a central side thereof and opposed to each other, a third side connecting one end of said first side and one end of said second side to each other, and a fourth side connecting said other end of said first side and said other end of said second side to each other;
   said first side and said second side are formed as a circular arc respectively in such a way that centers of said circular arcs are different from each other;
   a value relating to a groove depth ratio a (a=h1/h2) computed from a distance h1 between said impeller and said housing in said groove for hydrodynamic bearing of said portion in which a groove for hydrodynamic bearing is formed during a rotation of said impeller and from a distance h2 between said impeller and said housing in a groove for hydrodynamic bearing-non-present portion of said portion in which a groove for hydrodynamic bearing is formed during said rotation of said impeller is in a range of 1.5 to 2.5; and
   a value relating to a groove width ratio s (s=$B_0$/B) computed from a width $B_0$ of a peripheral portion of each groove for hydrodynamic bearing and a sum B (B=$B_0$+B1) of said width $B_0$ and a width B1 of a hydrodynamic bearing groove-non-present portion between peripheral portions of adjacent grooves for hydrodynamic bearing is in a range of 0.6 to 0.8.

8. A centrifugal blood pump apparatus according to claim 7, wherein said four corners of said groove for hydrodynamic bearing are rounded.

9. A centrifugal blood pump apparatus according to claim 7, wherein a plurality of grooves for hydrodynamic bearing is formed on said portion in which a groove for hydrodynamic bearing is formed;
   each of said grooves for hydrodynamic bearing has a first side and a second side both extending from a periphery of said portion in which a groove for hydrodynamic bearing is formed toward a central side thereof and opposed to each other, a third side connecting one end of said first side and one end of said second side to each other, and a fourth side connecting said other end of said first side and said other end of said second side to each other;
   said first side and said second side are formed as a circular arc respectively in such a way that centers of said circular arcs are different from each other; and
   four corners composed of said four sides are rounded.

10. A centrifugal blood pump apparatus according to claim 9, wherein said third side and said fourth side are formed as a circular arc respectively in such a way that said circular arcs have a same center and different radii.

11. A centrifugal blood pump apparatus according to claim 7, wherein said impeller has an upper shroud and a lower shroud, and said ring-shaped permanent magnet is embedded in the upper shroud.

* * * * *